US010449343B2

(12) United States Patent
Chang et al.

(10) Patent No.: US 10,449,343 B2
(45) Date of Patent: Oct. 22, 2019

(54) DEVICE FOR DISPENSING AND APPLYING A LIQUID

(71) Applicant: ACRUX DDS PTY LTD., Victoria (AU)

(72) Inventors: Shu Kuen Chang, Oakland, CA (US); Alain Regard, Beynost (FR); Anastasios G Karahalios, Chicago, IL (US); Mark LaFever, Indianapolis, IN (US)

(73) Assignee: ACRUX DDS PTY LTD, Victoria (AU)

( * ) Notice: Subject to any disclaimer, the term of this patent is extended or adjusted under 35 U.S.C. 154(b) by 429 days.

(21) Appl. No.: 15/039,156

(22) PCT Filed: Nov. 25, 2014

(86) PCT No.: PCT/US2014/067339
§ 371 (c)(1),
(2) Date: May 25, 2016

(87) PCT Pub. No.: WO2015/081078
PCT Pub. Date: Jun. 4, 2015

(65) Prior Publication Data
US 2017/0157378 A1    Jun. 8, 2017

Related U.S. Application Data

(60) Provisional application No. 61/909,274, filed on Nov. 26, 2013.

(51) Int. Cl.
*A61M 35/00* (2006.01)
*B05B 11/00* (2006.01)
(Continued)

(52) U.S. Cl.
CPC ......... *A61M 35/003* (2013.01); *A61K 9/0014* (2013.01); *A61K 31/568* (2013.01);
(Continued)

(58) Field of Classification Search
CPC .............. A61M 35/003; A61M 5/3271; A61M 5/3272; B05B 11/0032; B05B 11/3015;
(Continued)

(56) References Cited

U.S. PATENT DOCUMENTS 4,386,714 A    6/1983  Roberto et al.
5,152,427 A  * 10/1992  Pope .................. B65D 25/56
                                                                     116/200
(Continued)

FOREIGN PATENT DOCUMENTS

WO    WO-01/01813 A1    1/2001

OTHER PUBLICATIONS

International Search Report in PCT/US2014/067339 dated Feb. 12, 2015, 3 pages.
(Continued)

*Primary Examiner* — Tatyana Zalukaeva
*Assistant Examiner* — Jessica R Arble
(74) *Attorney, Agent, or Firm* — Hovey Williams LLP

(57) ABSTRACT

This invention relates to a device, a system and a method for applying a volume of liquid to a treatment surface. The device includes a container for containing the liquid, a pump for extracting liquid from the container, an actuator for operating the pump, and a collapsible receptacle for accommodating extracted liquid.

51 Claims, 9 Drawing Sheets

(51) Int. Cl.
  *A61K 9/00* (2006.01)
  *A61K 31/568* (2006.01)
  *A61K 47/10* (2017.01)
  *A61K 47/14* (2017.01)
  *A61K 47/32* (2006.01)
  *B05B 1/14* (2006.01)

(52) U.S. Cl.
  CPC .............. *A61K 47/10* (2013.01); *A61K 47/14* (2013.01); *A61K 47/32* (2013.01); *B05B 11/0032* (2013.01); *B05B 11/3015* (2013.01); *B05B 11/3052* (2013.01); *A61M 2202/04* (2013.01); *A61M 2210/00* (2013.01); *B05B 1/14* (2013.01); *B05B 11/3074* (2013.01)

(58) Field of Classification Search
  CPC ............. B05B 11/3052; B05B 11/3056; B05B 11/00416; A45D 34/04; B65D 83/00; B65D 83/0033
  See application file for complete search history.

(56) References Cited

U.S. PATENT DOCUMENTS

| | | | |
|---|---|---|---|
| 6,758,620 B1 | 7/2004 | Harrold | |
| 7,997,460 B2 | 8/2011 | Pardes et al. | |
| 8,118,509 B2 | 2/2012 | Marcellus | |
| 2005/0087191 A1* | 4/2005 | Morton | A61M 15/0065 128/205.23 |
| 2006/0032439 A1* | 2/2006 | Burato | A61M 35/00 118/712 |
| 2007/0267100 A1 | 11/2007 | Spear et al. | |
| 2008/0170904 A1* | 7/2008 | Bayly | A45D 34/04 401/265 |
| 2013/0181014 A1 | 7/2013 | Decottignies et al. | |
| 2014/0231464 A1* | 8/2014 | Cho | B05B 11/0038 222/321.8 |
| 2014/0270897 A1* | 9/2014 | Laurusonis | B05C 1/00 401/146 |
| 2016/0088921 A1* | 3/2016 | Jo | B05B 11/3052 222/173 |

OTHER PUBLICATIONS

Written Opinion of the International Searching Authority in PCT/US2014/067339 dated Feb. 12, 2015, 6 pages.

International Preliminary Report on Patentability and Transmittal in PCT/US2014/067339, dated Jun. 9, 2016, 8 pages.

\* cited by examiner

DEVICE FOR DISPENSING AND APPLYING A LIQUID

The present application is a U.S. National Stage of International Application No. PCT/US2014/067339 filed on Nov. 25, 2014, which claims the benefit of U.S. Provisional Application No. 61/909,274 filed on Nov. 26, 2013, the entire disclosures of all of which are incorporated herein by reference.

This invention relates to a device for dispensing and applying a volume of liquid to a treatment surface of a user. In further embodiments, the invention relates to a system for administration of a physiologically active agent and a method of transdermal administration using the device. The device is particularly, but not exclusively, suited for the application of a metered volume of transdermal or topical pharmaceutical, medicinal or therapeutic liquid to a skin surface of a user. It will be convenient to hereinafter describe the invention with reference to this preferred application; however, it is to be understood that the invention is not limited to this preferred application.

For the purpose of this specification the term liquid is intended to include all forms of non-viscous liquids, lotions, gels and creams.

It is generally understood that in order for a pharmaceutical, medicinal or therapeutic liquid (hereinafter liquid) to achieve a desired efficacy, it needs to be applied in accordance with the manufacturer's directions. This is particularly the case where the liquid is a medicated liquid intended to have a therapeutic effect at a certain dose of the active ingredient. Often in such cases, a specific volume of liquid will need to be applied to achieve the desired efficacy. If more than the specified volume of liquid is applied the user may suffer an adverse reaction, whereas if less than the specified volume of liquid is applied the desired efficacy may not be achieved.

Topical or transdermal liquids have previously been provided in squeezable containers or in containers with a finger operated pump. Such containers provide the user with a number of problems. For instance, it is very difficult for a user to dispense an accurate or measured volume from a squeeze container. Furthermore a finger operated pump requires the user to be capable of completing the stroke of the pump in order to accurately dispense the specified volume of liquid. In cases where the user makes an incomplete stroke, or multiple incomplete strokes, the pump may not dispense the required volume. Furthermore where a finger operated pump is supplied, inadvertent operation of the pump, while not in use can result in undesirable leakage of liquid. In either case of the squeeze container or pump, it can be difficult for the user to control the liquid as it is dispensed. A dispenser that facilitates dispensing the correct volume of liquid where a specified volume of liquid is required, and prevents leakage not in use would be desirable.

The manufacturer's directions often specify that the liquid should be dispensed into the palm of the user's hand for subsequent transfer to the treatment surface. In situations where the liquid is dispensed directly onto the treatment surface the liquid is often spread over the treatment surface using the palm of the hand, the fingers, the wrist or the forearm. This can result in residual liquid remaining on the user's hand(s) or arm(s) which is not ideal. Furthermore, this residual liquid can result in transference of the liquid via direct or indirect contact with objects, other people and animals. This can result in persons other than the user receiving treatment that they do not require, resulting in potentially harmful side effects with certain actives. It is generally desirable to limit application of the liquid to the treatment surface of the user only.

Devices have been designed to deposit topical liquids on the skin which do not require spreading or contact with the free hand. Some such devices dispense the liquid onto an applicator that is then used to spread the liquid over the treatment surface. This system of application suffers from the fact that the user has to physically transfer the liquid from the dispenser to the applicator before applying the liquid to the skin. Such a system is susceptible to a risk that the liquid will project from the pump or squeeze bottle, miss or splash from the applicator and land on the hand or body parts of the user.

Another type of dispenser system that is used to apply a topical liquid to the skin that does not involve a user initiated physical transfer of the liquid from the dispenser to the applicator, is a roll-a-ball type system is often used for applying anti-perspirants and deodorants to the axilla area of the body. The roll-a-ball is brought into contact with a bulk storage of the liquid which is transferred to the treatment surface of the user by rolling the ball across the treatment surface. This reduces the likelihood that liquid will be applied to, or reside on, parts of the body that are not intended to be treated. This type of applicator is not entirely satisfactory for medicated liquids as it is difficult to control the volume of liquid being applied.

Another issue with certain devices is inadvertent dispensing of the liquid by way of unintended operation of the pump. This can result in wasted liquid or even indirect transference if the liquid is dispensed over objects, unintended body parts, or animals which subsequently come into contact with other persons. Alternatively the pump may be operated by an unauthorised person, such as a child, which can lead to inappropriate dosing. It is generally desirable to try to limit use of the pump to intended and authorised use only.

A reference herein to a patent document or other matter which is given as prior art is not to be taken as an admission that that document or matter was known or that the information it contains was part of the common general knowledge as at the priority date of any of the claims.

According to one aspect of this invention there is provided a device for dispensing and applying a volume of liquid to a treatment surface, the device having an axis and including, a container for containing the liquid, a pump for extracting the volume of liquid from the container, an actuator for operating the pump, a receptacle defining a reservoir space while accommodating the extracted volume of liquid which substantially collapses when the volume of liquid is applied to the treatment surface, the receptacle having an aperture formed in a floor thereof through which the volume of liquid enters the reservoir space.

The receptacle may include a wall surrounding the floor, at least the wall of the receptacle is resiliently deformable so that in an erect condition it defines at least in part the reservoir space and resiliently deforms when the receptacle collapses. The floor and wall may be formed from a thin membrane. The pump may include a head and a body with the head being movable in the direction of the axis so as to induce the volume of liquid to be expelled out of the head of the pump, the floor of the receptacle being resiliently deformable and operatively associated with the pump head so as to deform when the head is moved. The head may be movable towards the body when inducing the volume of liquid to be expelled out of the head of the pump. The reservoir space has a depth, and it is preferred that the floor of the receptacle is movable with the pump head so that the depth of the reservoir space increases when the head is moved towards the body. This preferred arrangement reduces the likelihood that the liquid will inadvertently egress from the reservoir space while the pump dispenses the liquid.

The device preferably includes a diffuser which diffuses the liquid as it enters the reservoir space. The diffuser may take any suitable form and one form may include a single inlet and multiple outlets to guide the liquid across the floor of the reservoir space. It is preferred that the outlets are oriented relative to the inlet so as to cause the liquid to change direction as it travels from the inlet to the outlets. These preferred features further control the dispensing of liquid from the pump, reducing the likelihood that the liquid will inadvertently egress from the reservoir space.

The actuator may include a base which is fixed relative to the container, a rotatable member that is rotatable relative to the base, and a shuttle that operatively interacts with the pump, and rotates with the rotatable member, and moves relative to the base in the axial direction when the pump extracts the volume of liquid. The device may include a rack and pawl mechanism associated with the rotatable member and the base configured to hinder the rotation of the rotatable member in a non-preferred direction. It is preferred that the rack and pawl mechanism is configured to cause a greater level of hindrance to rotation of the rotatable member in the non-preferred direction when the actuator is in a rest position. This may be achieved in any suitable manner which may include the rack including a plurality of teeth of one size and one tooth that has a larger trailing edge, wherein the interaction of the pawl with the larger trailing edge causes said greater level of hindrance. The larger trailing edge is preferably at least 40% greater in depth than a trailing edge of a majority of the teeth.

The actuator may include a cam means so that rotation of the rotatable member causes axial movement of the shuttle from a first position toward a second position. The cam means may include a cam surface on the shuttle and a cam follower on the base, wherein the cam follower moves along the cam surface on rotation of the rotatable member. It is preferred that the cam surface is configured to interact with the follower so as to reduce resistance on the shuttle returning to the first position as the actuator approaches a rest position. This may be achieved in any suitable manner and one arrangement may include the cam surface is shaped with an end portion which is aligned substantially vertically so as to permit the shuttle to return to the first position before the actuator reaches the rest position. This preferred arrangement reduces the resistance on the head of the pump returning to a closed position.

The shuttle and rotatable member may include guide means to limit movement of the shuttle relative to the rotatable member to movement in the axial direction. The device may include a stop means for preventing the shuttle from moving in the axial direction unless by way of rotation of the rotatable member.

The pump is preferably a positive displacement pump and the container includes a relatively rigid outer shell and a relatively collapsible inner lining, whereby the liquid is retained in the lining which collapses upon operation of the pump.

According to another aspect of this invention there is provided a device for dispensing and applying a volume of liquid to a treatment surface, the device including: a container for containing the liquid, a pump for extracting the volume of liquid from the container, an actuator for operating the pump, a receptacle defining a reservoir space for accommodating the extracted volume of liquid, the receptacle is used to apply the liquid to the treatment surface, a cap that covers the receptacle and prevents operation of the actuator when in a closed position and, when in an open position reveals the receptacle and permits operation of the actuator, a latch that interacts with the cap so that in a latch condition retains the cap in the closed position and can be adjusted to a release condition to allow the cap to be moved to the open position.

The device may include a base that is fixed relative to the container which includes the latch, whereby the base is configured to resiliently deform to adjust the condition of the latch between a latch condition and a release condition. The latch may include a pair of tabs on opposed sides of the base, and the base includes a deformation zone adjacent each tab which is resiliently deformable for adjusting the condition of the latch. The cap may include a pair of apertures formed adjacent an open end of the cap at opposed sides thereof, whereby each aperture receives one of the tabs when the cap is in the closed position and the latch is in the latch condition. The base may include a seat zone for accommodating the open end of the cap, the seat zone being sized to accommodate the open end of the cap in a friction fit. The seat zone includes an annular wall which engages an inner surface of the cap adjacent the open end, the inner surface overlapping with the annular wall so as to produce the friction fit. The inner surface of the cap may overlap with the annular wall so as to prevent tilting of the cap relative to the base. The inner surface of the cap may overlap with the annular wall so as to require the cap to be moved in an axial direction when moving to the open position. It is further preferred that both deformation zones be depressed to move the cap to the open position. This preferred aspect reduces the likelihood that the cap will be inadvertently removed from the base, and in particular removed by a child. It is still further preferred that the actuator includes a rotatable member that rotates relative to the base to operate the pump, wherein the cap prevents rotation of the rotatable device when the cap is in the closed position. This preferred arrangement reduces the likelihood that the pump will be inadvertently operated.

The receptacle may be resiliently deformable so as to collapse when applying the liquid to the treatment surface and deforms when the actuator is operated. The receptacle may be resiliently deformable to collapse when spreading the liquid over the treatment surface. The receptacle may include a wall surrounding a floor, whereby when the wall is in an erect condition it defines at least in part the reservoir space and resiliently deforms when the receptacle collapses. The floor and wall are formed from a thin membrane.

The treatment surface may be any suitable area however it is preferred that the area is an axilla area of a user's skin.

The container may contain any suitable liquid and one preferred liquid is in the form of a composition including a physiologically active agent. It is further preferred that the physiological active agent includes at least one agent selected from steroidal hormones and non-steroidal anti-inflammatory drugs.

According to another aspect of this invention there is provided a device for dispensing and applying a volume of liquid to a treatment surface, the device having an axis and including: a container for containing the liquid, a pump for extracting the volume of liquid from the container, an actuator for operating the pump, a receptacle defining a reservoir space while accommodating the extracted volume of liquid which substantially collapses when the volume of liquid is applied to the treatment surface, the receptacle having an aperture formed in a floor thereof through which the volume of liquid enters the reservoir space, wherein the reservoir space has a depth, and the floor of the receptacle is movable with operation of the pump head so that the depth of the reservoir space increases while the liquid enters the reservoir space.

In accordance with a further aspect there is provided a system for transdermal administration of a physiologically active agent from a liquid, the system comprising a device as hereinbefore described wherein the container contains a liquid composition comprising a physiologically active agent.

In accordance with a further aspect there is provided a method of transdermal administration of a physiologically active agent to a subject including providing a device as herein described wherein a liquid comprising the pharmaceutically active agent is contained in the container; pumping a volume of liquid from the container through the aperture formed in a the receptacle to the receptacle defining a reservoir space to accommodate the extracted volume of liquid wherein the reservoir space is adapted to substantially collapse when the volume of liquid is applied to the treatment surface; spreading the liquid over an area of skin in at least one axilla of the subject.

In accordance with a further set of embodiments there is provided a method of dispensing a volume of liquid for application to a skin surface including: providing a device as herein described comprising a container containing the liquid, pumping a volume of liquid from the container through the aperture formed in a the receptacle to the receptacle defining a reservoir space to accommodate the extracted volume of liquid wherein the reservoir space is adapted to substantially collapse when the volume of liquid is applied to the treatment surface.

It will be convenient to hereinafter describe the invention in greater detail by reference to the attached illustrations which show a preferred embodiment of the various aspects of this invention. The particularity of those drawings and the related detailed description is not to be understood as superseding the generality of the proceeding description of the invention according to each of its aspects.

In order that the invention may be more fully understood, some embodiments will now be described with reference to the figures in which:

BRIEF DESCRIPTION OF THE DRAWINGS

FIG. 3a is a schematic detail of the teeth of the rack from FIG. 3 with the collar in a rest position.

DETAILED DESCRIPTION OF THE DRAWINGS

Figure 1:
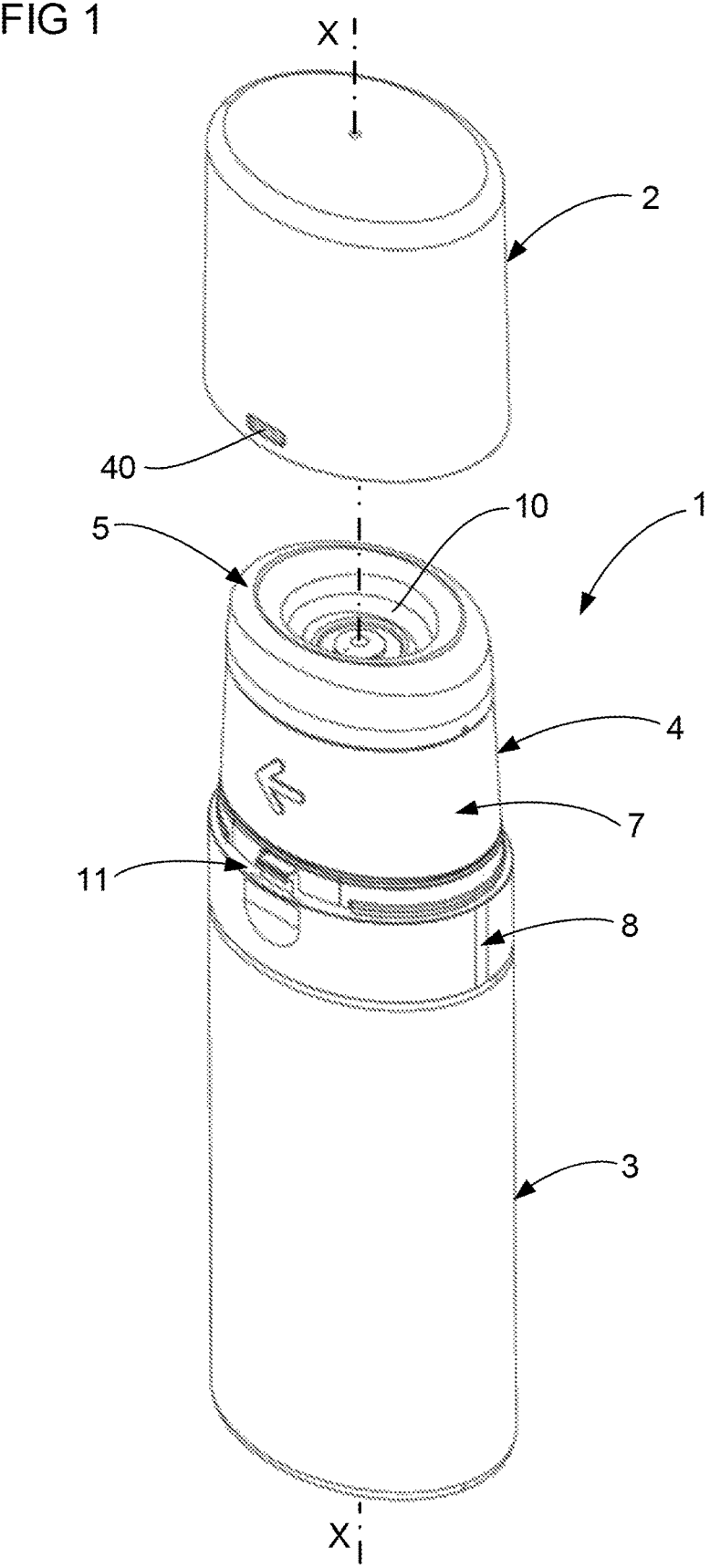
FIG. 1 is an isometric view of a preferred embodiment of the device according to one aspect of the invention.

FIG. 1 illustrates a preferred embodiment of the device 1 according one aspect of the invention. The device 1 includes a cap 2 which is shown in a detached position, a container 3, an actuator 4 in a rest position and an empty receptacle 5. The device 1 is designed for dispensing a volume of liquid to the receptacle 5, and using the receptacle 5 to spread the liquid over a treatment surface 6 (see FIG. 9). The receptacle 5 may take any shape in order to receive and spread the liquid and the invention is not limited to a receptacle 5 of the shape as illustrated in FIG. 1. The treatment surface 6 may be any surface designated by the user and this includes a skin surface of the user. The device 1 is particularly suited to apply liquid to an axilla area of the user's skin, however the invention is not limited to application in this area only. It is preferred that the reservoir space 10 be within a range of 2 ml to 20 ml, with approximately 5 ml being most preferred when the liquid dispensed contains a drug.

FIG. 1 illustrates a preferred form of actuator 4 including a rotatable collar 7 and a base 8. The base 8 is fixed in position relative to the container 3 whereas the collar 7 is rotatable (in the direction of the arrow) relative to the base 8 about the axis X-X shown in FIG. 1. This rotation causes operation of the pump 9 (see FIG. 2). The pump 9 forces liquid out of the container 3 and into a reservoir space 10 defined by the receptacle 5. FIG. 1 also illustrates a preferred form of part of a latch 11 which interacts between the cap 2 and the base 8 to retain the cap 2 in a closed position (see FIG. 4). The other features of the actuator 4 will be described in greater detail by reference to the later illustrations. The function of the actuator 4 is to facilitate operation of the pump 9. It should be appreciated that the actuator 4 may take any suitable form and the invention is not limited to the form described in this detailed description and illustrated in the attached figures.

The container 3 may take any shape and is not limited to the shape of a bottle as illustrated in the figures. Furthermore the container 3 may directly contain the liquid, or indirectly containing the liquid, by for example way of a bag (not shown) of liquid within the container. Where the device 1 is applying a drug in liquid form, it is desirable for the liquid to be contained within a bag. The bag may reduce in volume as the liquid is dispensed to reduce the likelihood of the air spoiling the drug. While part of the function of the container 3 is to contain, directly or indirectly, the liquid, another function of the container 3 is to provide a handle for the user to grip while operating the actuator 4.

Figure 2:
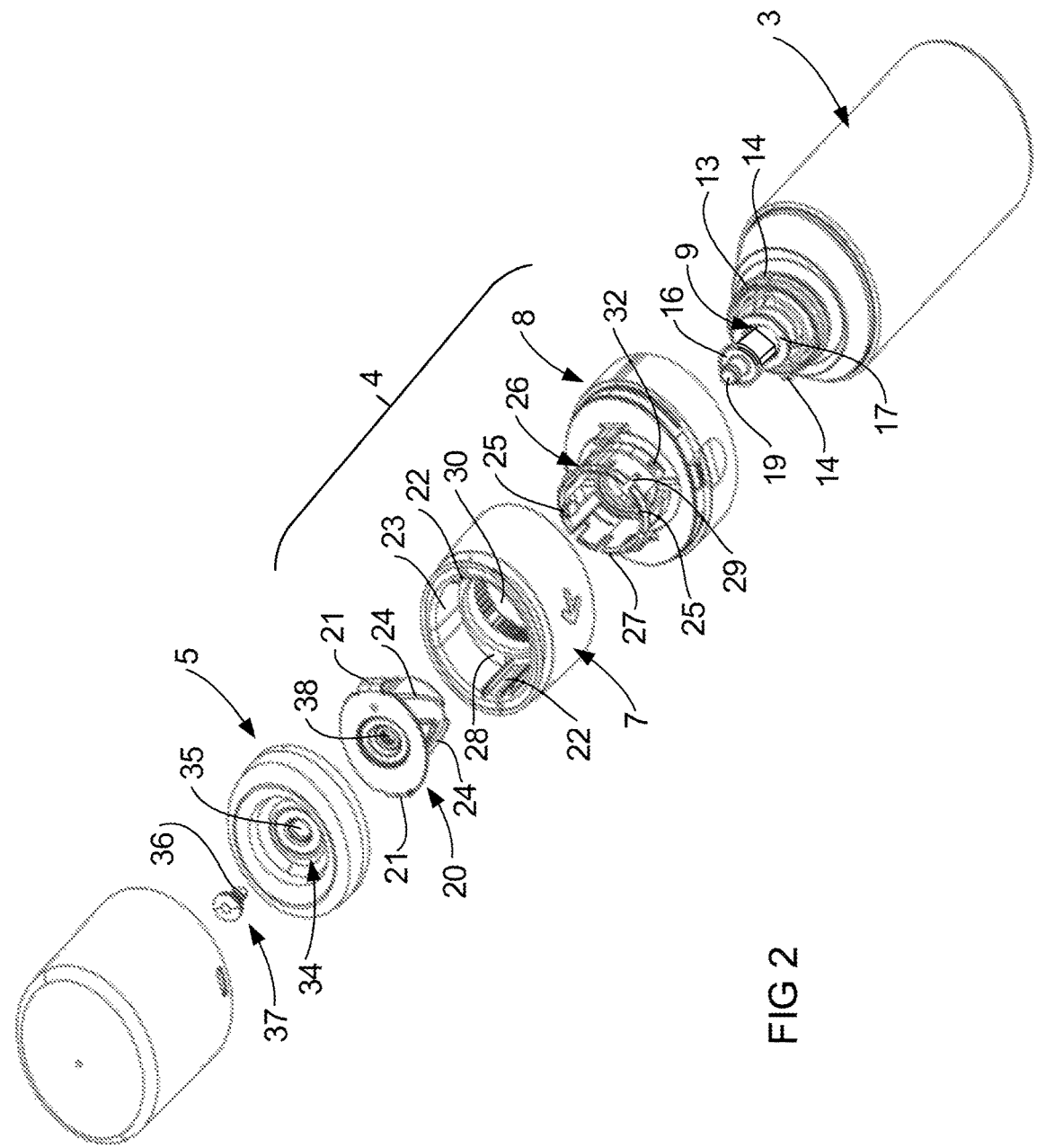
FIG. 2 is an exploded view of the preferred embodiment from FIG. 1.
Figure 3:
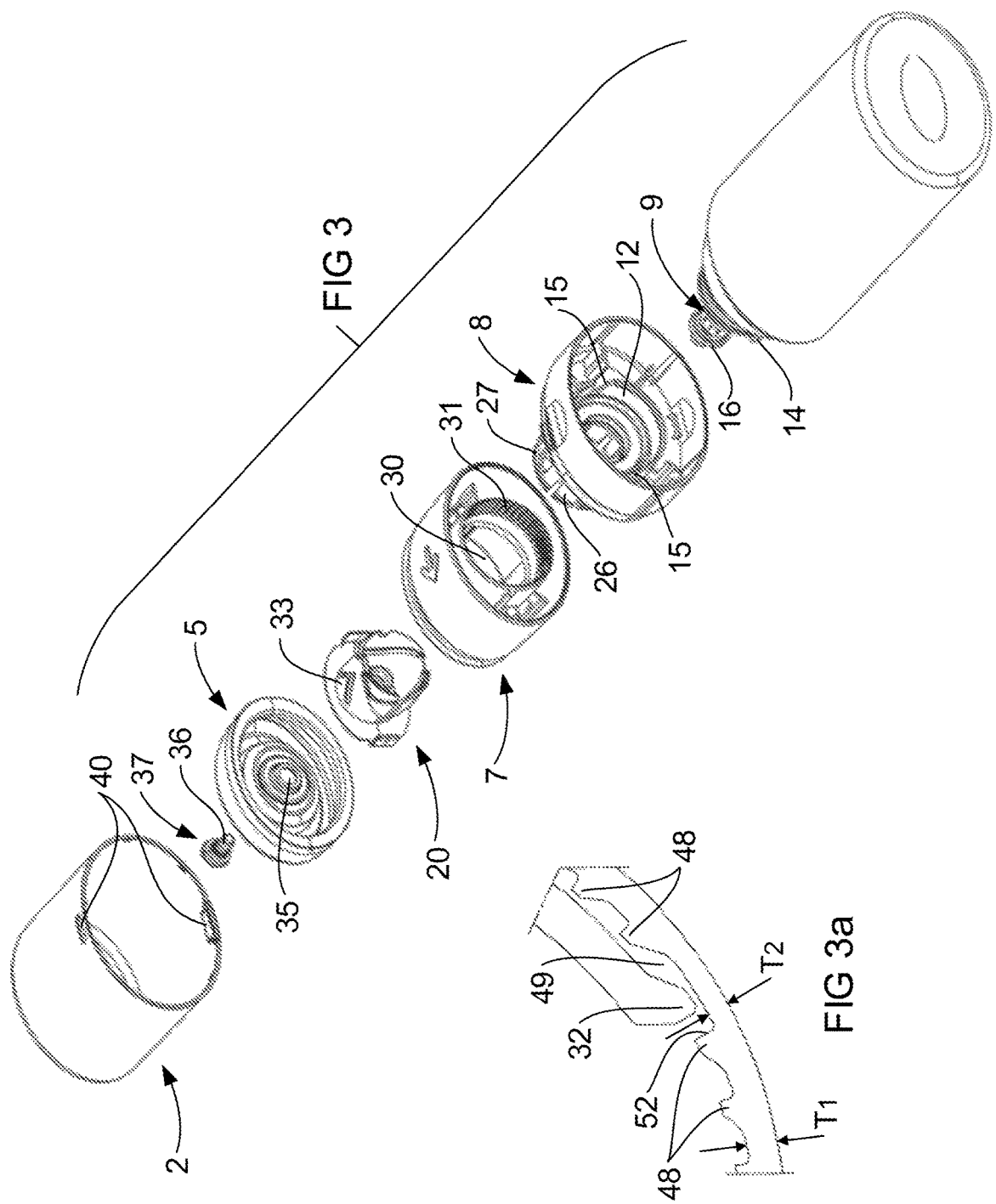
FIG. 3 is a reverse exploded view of the embodiment from FIG. 2.
Figure 4:
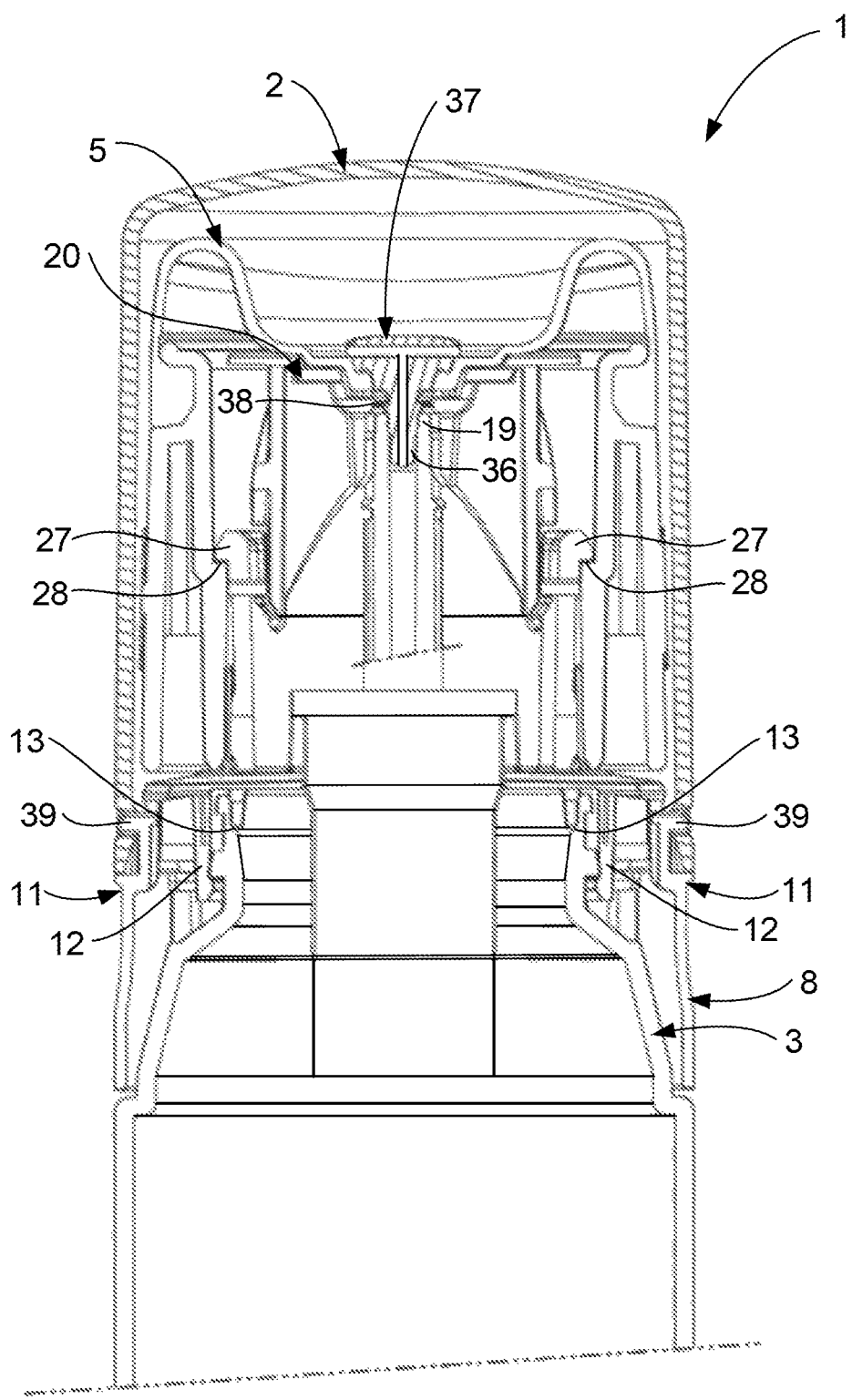
FIG. 4 is a cross sectional view of a portion of the device with the cap in a closed position and a latch in a latched condition.

Referring now to FIG. 2 which illustrates the base 8 spaced from the container 3, the base 8 preferably snap fits onto the container 3 by interaction of annular projecting portions 12 of the base 8 with annular projecting portions 13 of the container 3 (see FIG. 4). The snap fit is preferably designed to allow for easy assembly of the device 1, while providing a relatively permanent connection between the base 8 and the container 3. The annular projecting portion 13 of the container 3 also includes a pair of opposed locating lugs 14 (see FIG. 2), which locate in slots 15 (see FIG. 3) formed in the annular projecting portion 12 of the base 8.

The lug 14 and slot 15 arrangement helps locate the base 8 on the container 3 while preventing rotation of the base 8 relative to the container 3. It should be appreciated that the location of the lugs 14 and slots 15 could be reversed while still achieving the same function. Furthermore the location of the lugs 14 and the slots 15 on the base 8 and container 3 respectively may vary from the positions as shown in the illustrations.

Figure 5:
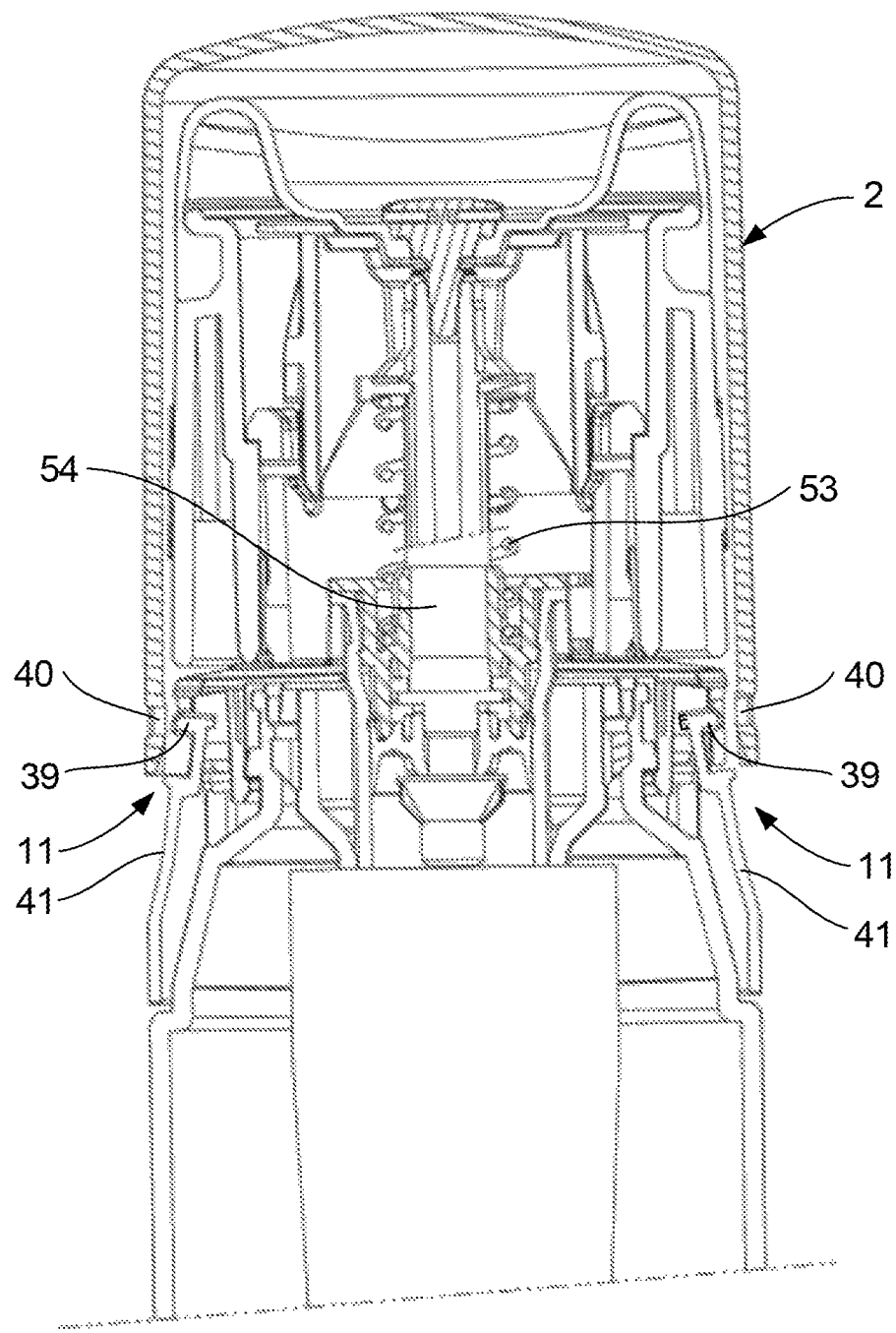
FIG. 5 is the preferred embodiment from FIG. 4 with the latch in the release condition.

The pump 9 illustrated in FIG. 2 includes a pump head 16 and the pump body 17. The pump head 16 is often referred to in the industry as a pump stem and for the purposes of this specification the terms pump head and pump stem are interchangeable. A spring 53 (See FIG. 5) acts between the head 16 and the body 17 to urge the head 16 away from the body 17. Movement of the head 16 towards the body 17 causes operation of the pump 9 by pressurising the liquid contained within the container 3, forcing a metered quantity of the liquid into a pump chamber 54 (see FIG. 5) and out through an outlet 19 in the head 16 of the pump 9. Thereafter the spring 53 returns the head 16 to the rest position to re-fill the pump chamber 54 with liquid from the container 3. The action of returning the head 16 to the rest position also seals the pump head 16 which inhibits evaporation of liquid from the pump chamber 54, and leakage of liquid from the pump chamber 54 back into the container 3. This facilitates ensuring the pump chamber 54 remains filled with the correct dose of liquid for when the pump 9 is next operated. The action of returning the head 16 back to the rest position is as a result of force applied by the spring 53. Whilst it is desirable for the force be sufficient to return the head 16 to the rest position, that force must not be too great to prevent a user from depressing the head 16.

The preferred form of pump 9 is a positive displacement pump as it is capable of providing a specified volume of liquid, however other forms of pump may also be suitable. The function of the pump 9 is to dispense liquid from the container and it is preferred that this be achieved in an accurate and repeatable manner. Clearly other forms of pump may be suitable and the invention is not limited to the form of pump described in this detailed description and illustrated in the attached figures. Not all features of the pump body 17 are illustrated in the FIGS. 4 to 8, as the invention is not to be limited to a pump having specific internal components. The internal components may vary to suit the needs of the liquid to be dispensed.

FIG. 2 also illustrates a shuttle 20 which forms part of the actuator 4, which in use is located within the collar 7. The shuttle 20 includes a pair of shoulders 21 on opposed sides thereof which locate in slots 22 formed in an inner wall 23 of the collar 7. The shoulders 21 and slots 22 arrangement ensure the shuttle 20 rotates with the collar 7, while limiting relative movement between the shuttle 20 and collar 7 to movement in the axial direction that is along axis X-X. This axial movement is achieved by a cam surface 24 formed on the shuttle 20 interacting with a cam follower 25 formed on the inside surface of a neck portion 26 of the base 8. FIG. 2 illustrates the shuttle 20 having a pair of opposed cam surfaces 24 and the neck 26 having a pair of opposed cam followers 25 which is preferred to balance the forces acting on the shuttle 20. Rotation of the collar 7 causes rotation of the shuttle 20 about the axis X-X also, which causes the cam surface 24 to move over the cam follower 25. The cam surface 24 is ramped so that rotation of the collar 7 through 90° from the rest position illustrated in FIG. 1 moves the shuttle 20 completely down to fully depress the pump head 16 towards the pump body 17. This movement of the head 16 is against the force of the spring 53 and results in a dose of liquid being dispensed from the container to the receptacle. Continued rotation of the collar 7 through a further 90° moves the cam follower 25 over the cam surface 24 to allow return of the shuttle 20 to the rest position with the assistance of the spring 53. This results in the pump chamber 54 being refilled as previously described.

The collar 7 is preferably retained by the base 8 by snap fitting onto the base 8. The preferred embodiment illustrated in FIGS. 2 and 3 has a free end of a neck 26 of the base 8 including a lug formation 27 about the perimeter thereof. A ledge formation 28 (see FIG. 2) on the inner surface of the collar 7 interacts with the lug formation 27 (see for example FIG. 4). The neck portion 26 of the base 8 includes vertically extending notches 29 adjacent the free end so as to allow the perimeter of the free end to contract when fitting through an opening 30 (see FIG. 3) in the collar 7. This allows the neck 26 to resiliently deform until such time as the lugs 27 locate over the ledge 28 formed in the collar 7 (see FIG. 4).

It is generally desirable to control movement of the pump 9 head 16 relative to the body 17, so as to ensure the pump 9 dispenses the correct metered volume of liquid. This may be achieved by any suitable arrangement and in the embodiment illustrated rotation of the collar 7 is limited to one direction only. More specifically, the device 1 is designed so as to inhibit rotation of the collar 7 against the direction of the arrow on the collar 7. FIG. 2 illustrates the collar 7 being formed with the arrow on an outer surface thereof to indicate the direction of movement of the collar 7 relative to the base 8. It can be appreciated from FIG. 3 that the collar 7 has a rack formation 31 around the opening 30. This rack formation 31 interacts with a flexible detent or pawl 32 formed on the neck 26 of the base 8 so as to function as a ratchet. The detent or pawl 32 slides over the rack formation 31 as the collar 7 is rotated in the direction of the arrow. The pawl will lock into the rack formation 31 if attempts are made to rotate the collar 7 against the direction of the arrow. This prevents the collar 7 being rotated back and forth to dispense more than the intended amount. Instead the user is limited to rotating the collar 7 in one direction only.

It is preferred that the rack formation 31 be configured to create a greater level of hindrance to rotation of the collar 7 against the direction of the arrow when the actuator is in a rest position. This may be achieved in any suitable manner and in the embodiment illustrated the rack 31 has thickness T1 between the majority of the teeth 48, and a thickness T2 at a location that the pawl 32 seats in when the actuator 4 is in the rest position (see FIG. 3a). This creates a tooth 48 with a larger trailing edge 52 that creates a greater barrier to the pawl 32 if the collar 7 was to be rotated against the direction of the arrow from the rest position. This trailing edge 52 may be up to 40% larger than the trailing edge of the remainder of the teeth 48. Furthermore when the pawl 32 moves over the larger trailing edge 52 it may also provide a tactile indicator to the user to indicate the collar 7 has reached the rest position.

It can also be appreciated from FIG. 3a that there is clearance under the pawl 32 when located in the trough 49. This removes the load from the pawl 32 that it experiences when traveling over the remainder of the teeth 48. This reduces the likelihood of the pawl 32 from permanently deforming over time if it remained under load, which is a particular issue when the pawl 32 (or whole base 8) is formed from a plastics material referred to as plastic creep.

It is generally desirable that the shuttle 20 be prevented from operating the pump 9 other than by way of rotation of the collar 7. In this regard FIG. 3 illustrates the shuttle 20 being formed with a V-shaped formation 33 on an outer surface thereof, with a corresponding formation on an opposed side of the shuttle 20 (obscured). The V-shaped formation 33 is aligned to abut the cam follower 25, if directly depressed, when the actuator 4 is in the rest position shown in FIG. 2. It ought to be appreciated that once the collar 7 is rotated relative to the base 8, the V-shaped formation 33 is moved out of alignment with the cam follower 25 so as to allow the shuttle 20 to depress the head 16 of the pump 9.

FIG. 2 also illustrates a floor portion 34 of the receptacle being formed with a centrally located aperture 35. The aperture 35 receives a shaft portion 36 of a diffuser 37 of the device 1. The shaft portion 36 also extends through a central bore 38 in the upper surface of the shuttle 20 to locate within the outlet 19 of the pump 9 (see FIG. 4). This attaches a central zone of the floor portion 34 of the receptacle 5 to the shuttle 22, so that at least the floor portion 34 of the receptacle 5 moves with the shuttle 20 in the axial direction along axis X-X when the collar 7 is rotated. This movement of the floor portion 34 of the receptacle 5 will be described in greater detail with reference to latter illustrations.

FIG. 4 illustrates a portion of the device 1 in cross section with the cap 2 in a closed position. The latches 11 on opposed sides of the base 8 are shown in the latch condition. The latches 11 include tabs 39 illustrated located in opposed apertures 40 (see FIG. 3) formed adjacent the open end of the cap 2. When comparing FIG. 4 with FIG. 5, it can be appreciated that each of the tabs 39 have been moved out of the apertures 40 formed on opposed side of the cap 2. The latch is considered to be in a release condition when the tabs 39 are moved out of the apertures 40. This allows the cap 2 to be moved axially towards the open position as shown in FIG. 1. The movement of the tabs 39 is achieved by the user simultaneously applying pressure on deformation zones 41 of each latch. The tolerance between the cap 2 and the base 8 is such as to require simultaneous pressure on the deformation zones 41 to allow the tabs 39 to disengage from the apertures 40. More specifically movement of either tab 39 only will not permit removal of the cap 2 from the base 8. Furthermore the latches are formed so as to require a force of in the range of 20N to 40N acting on both depression zones before the latches 11 will release. Finally the location of the latches 11 on opposed sides of the base 8 is merely preferred for safety reasons, however the latches 11 may be located elsewhere on the base. These features have been considered within the capacity of the likely adult user population, while inhibiting use of the device 1 by children.

Once the pressure is released from the deformation zones 41, the resilient nature of the material forming the deformation zone 41 allows the tabs 39 to return to the positions illustrated in FIG. 4. Once the device 1 has been used by the user, the cap 2 can be returned to the closed position by moving it down in the axial direction to snap lock over the tabs 39 of the latch 40.

Figure 6:
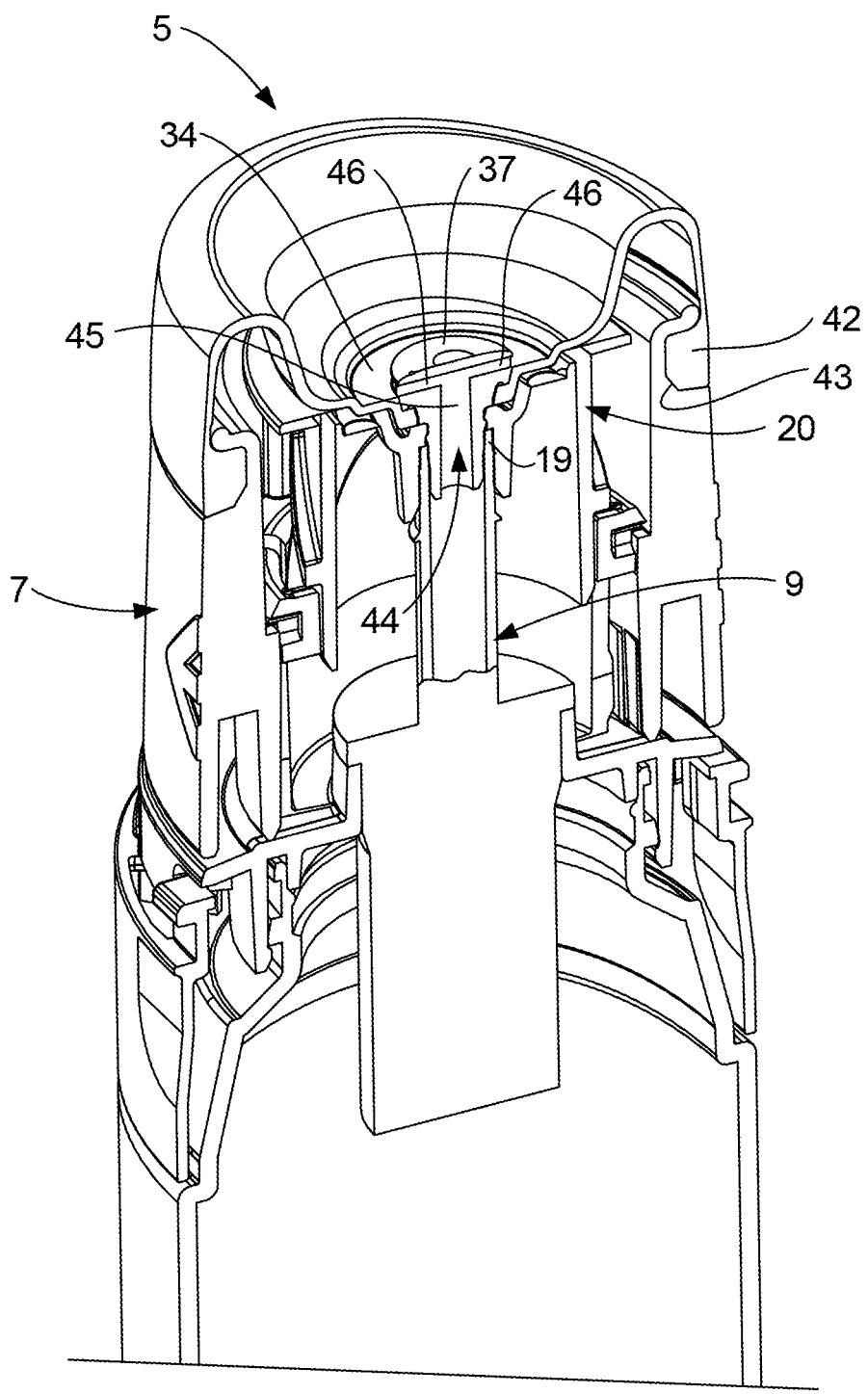
FIG. 6 is a sectional isometric view of a portion of the device with the cap detached.

Referring now to FIG. 6, it can be appreciated that an outer rim 42 of the receptacle 5 is located in a recess 43 formed in an upper surface of the collar 7. Furthermore, the floor portion 34 of the receptacle 5 is seated on an upper surface of the shuttle 20 and attached thereto by the diffuser element 37. The shaft of the diffuser element 37 extends through the receptacle 5 and engages the outlet 19 of the pump 9 in a snap fit. The diffuser 37 defines a conduit 44 to allow the egress of liquid from the pump 9 outlet 19 to spread over the floor 45 of the receptacle 5. The conduit 44 is initially formed by a single passageway 45 extending in the axial direction towards the top of the diffuser 37. The conduit 44 changes from the single axial passageway 45 to multiple passageways 46 that extend in a radial direction, substantially parallel to the floor 34 of the receptacle 5. The change from a single passageway 45 to multiple passageways 46, and change in direction of the conduit 44 is designed to reduce the speed of the liquid exiting the diffuser 37 and reduce the likelihood of spillage from the receptacle 5.

Figure 7:
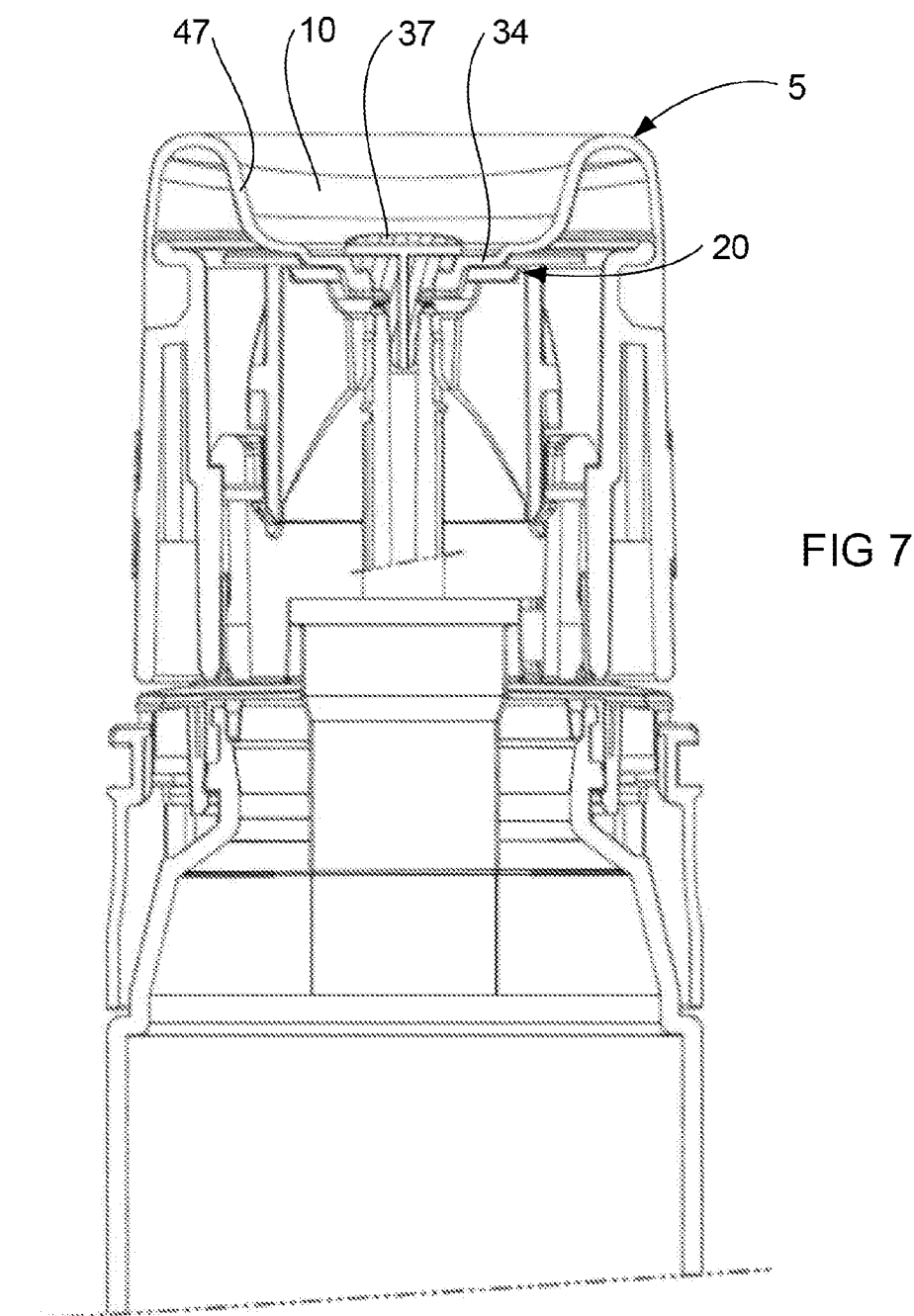
FIG. 7 is a cross sectional view of a portion of the device with the actuator in a rest condition.
Figure 8:
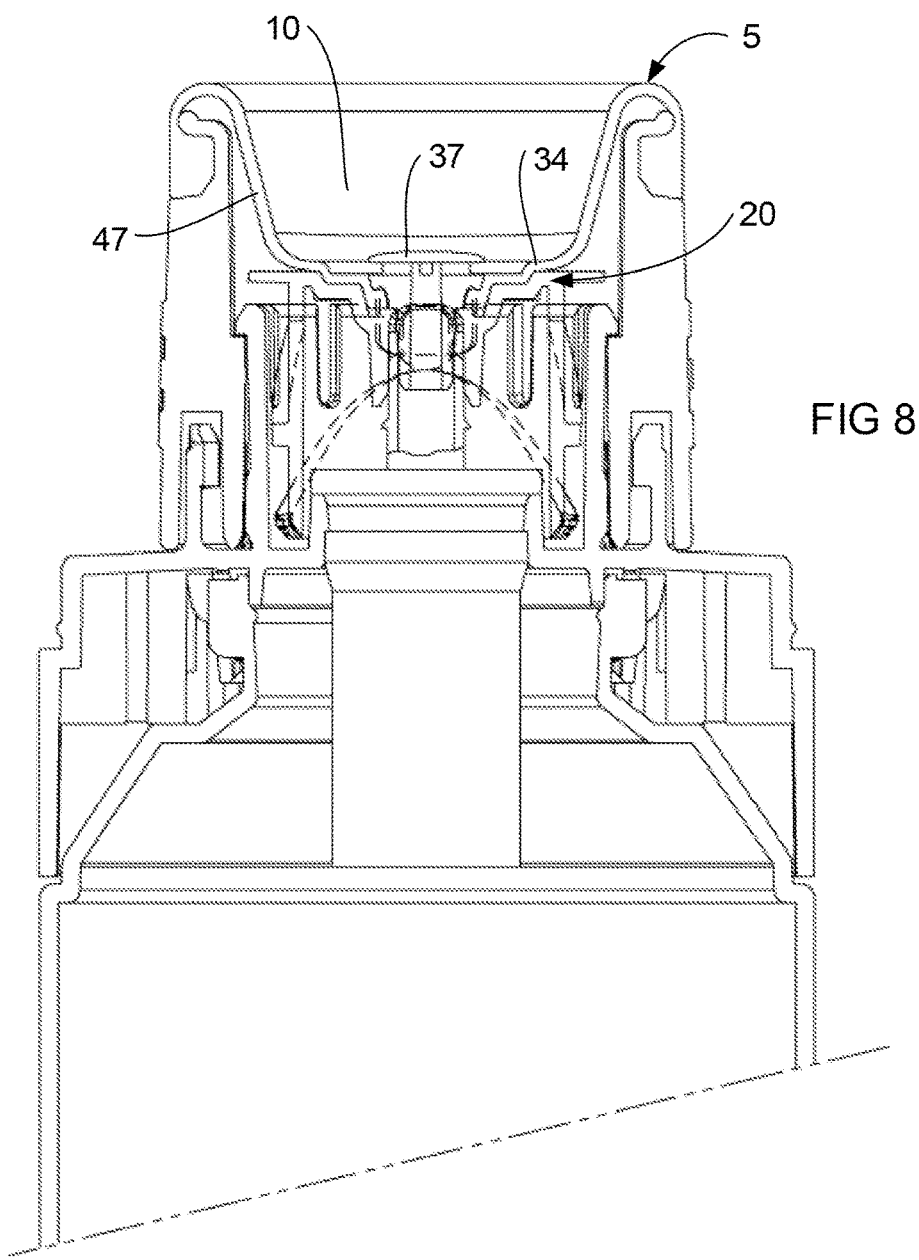
FIG. 8 is a cross sectional view of the device with the actuator rotated through 90° relative to the base.

It can be appreciated by comparing FIGS. 7 and 8 that when the shuttle 20 is depressed as illustrated in FIG. 8, it draws the floor 34 of the receptacle 5 down to increase a depth of the reservoir space 10 from the upper rim 42. Also the wall 47 extending between the floor 34 and the rim 42 changes shape. A radius of curvature of an upper portion of the wall 47 is reduced and the length of the wall 47 stretched so as to increase the volume of the reservoir space 10. The receptacle 5 is of an oval shape and it is preferred that the wall thickness 47 vary so that the change in shape of the receptacle 5 is uniform. It is during this time that the liquid is dispensed out through the diffuser 37 into a relatively deep reservoir space 10. The deep reservoir space 10 in conjunction with the uniform deformation of the receptacle reduces the likelihood of spillage of liquid over the wall 47 of the receptacle 5. Upward movement of the shuttle resulting from further rotation of the collar 7 returns the floor 34 of the receptacle 5 back to the position as illustrated in FIG. 7 preparing the device 1 for application of the liquid to the treatment surface 6.

Figure 9A:
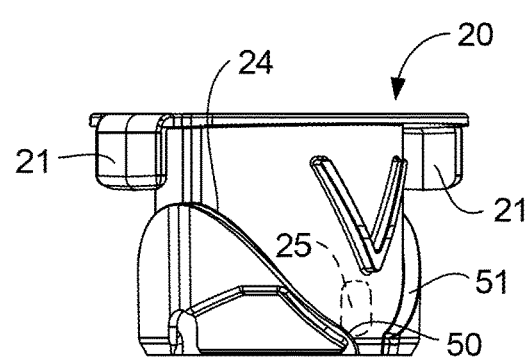
FIG. 9a is a schematic elevation view of the shuttle and follower as the collar approaches the rest position.
Figure 9:
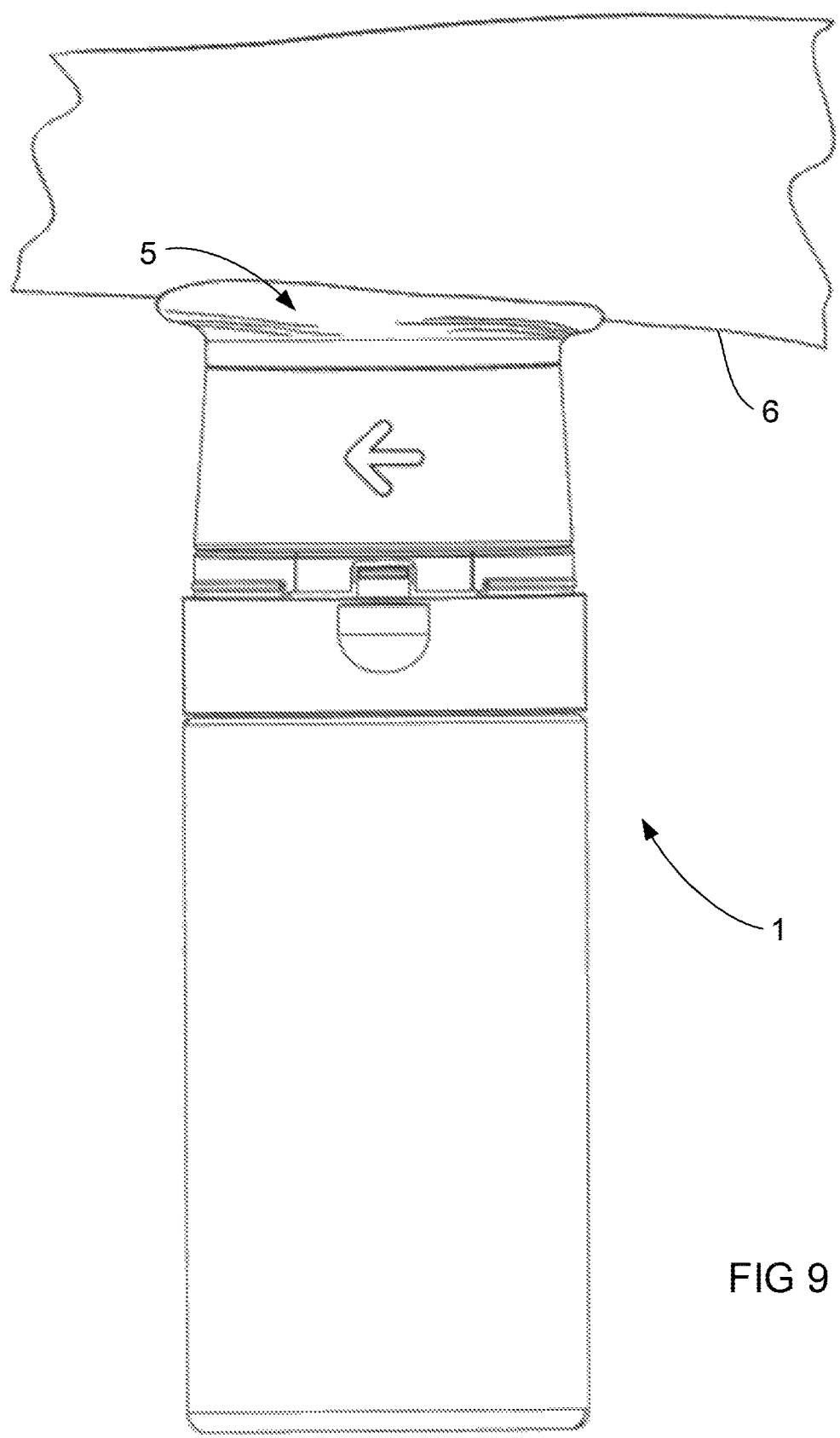
FIG. 9 is a front elevation view of the device in use.

The application of the liquid from the reservoir space 10 onto the treatment surface 6 is illustrated in FIG. 9. It is to be appreciated from this figure that the receptacle 5 is collapsible under the pressure of forcing the receptacle 5 onto the treatment surface 6. This reduces the overall depth of the reservoir space 10 and facilitates effective transfer of all the liquid from the receptacle 5 to the treatment surface 6. The collapse of the receptacle 5 is significant to the extent that it is substantially incapable of retaining liquid in the reservoir space 10 thereafter. Furthermore, the flexible nature of the receptacle 5 enhances the ability of the device 1 to spread the liquid over the treatment surface 6, and reduces the likelihood that liquid will remain in the reservoir space 10 after spreading.

The receptacle 5 may be formed from any suitable material provided that that material is resiliently deformable and liquid impervious. One preferred form of material is silicone. However, it may also be formed from a natural or synthetic rubber or coated polymer materials. It can be appreciated from at least FIG. 8 that the receptacle 5 is preferably formed with a relatively thin membrane forming the floor 34 and wall 47 of the receptacle 5. The receptacle 5 may be formed in any suitable manner, however it is preferred it is formed by molding.

Figure 7A:
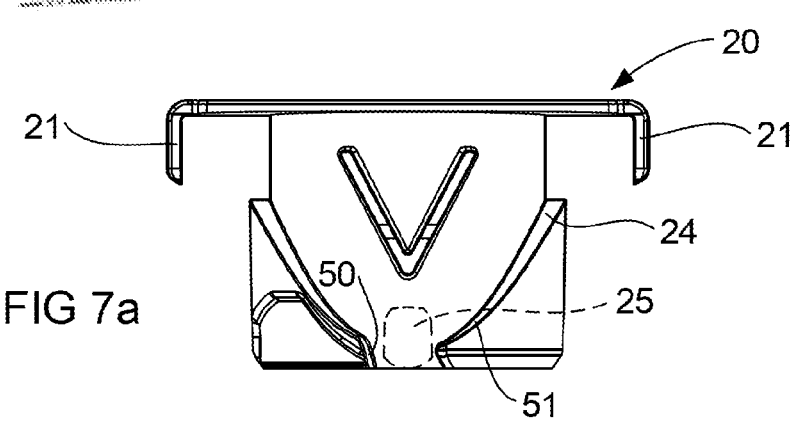
FIG. 7a is a schematic elevation view of the shuttle and follower corresponding to the position illustrated in FIG. 7.
Figure 8A:
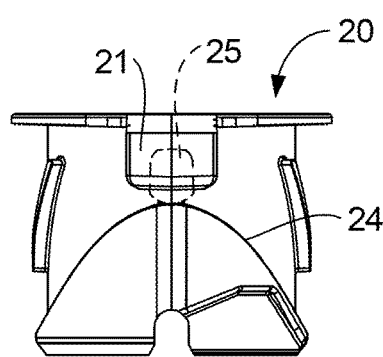
FIG. 8a is a schematic elevation view of the shuttle and follower corresponding to the position illustrated in FIG. 8.

The cam surface 24 is preferably configured to interact with the follower 25 so as to reduce resistance on the shuttle 20 as the actuator 4 approaches the rest position. FIG. 7 illustrates the actuator 4 in the rest position while FIG. 7a illustrates schematically the interaction of the cam surface 24 with the follower 25 (with the base 8 not shown for clarity). The shuttle 20 is illustrated in a raised position relative to the base 8 so as to position the follower 25 at the start of the cam surface 24. FIG. 8 illustrates the collar 7 having been rotated clockwise through 90°, and FIG. 8a illustrates schematically the shuttle 20 having been rotated with the collar 7. This results in the follower 25 (shown in dotted line behind the shoulders 21) sliding along to an apex of the cam surface 24. FIG. 9a illustrates the shuttle 20 having been further rotated clockwise through less than 90°, with the actuator 4 approaching the rest position. It should be noted that FIG. 9a illustrates the cam surface 24 having an end portion 50 that is aligned more vertically than the start 51 of the cam surface 24 as illustrated in FIG. 7a. The follower 25 is illustrated approaching the end portion 50 and it can be appreciated that the shuttle 20 will move vertically more easily (under the influence of the pump spring 53), allowing the pump head 16 to seal the pump chamber 54, before the collar 7 has completed its rotation to the rest position.

In one set of embodiments there is provided a system for transdermal administration of a physiologically active agent from a liquid, the system comprising a device as hereinbefore described wherein the container contains a liquid composition comprising a physiologically active agent.

In a preferred set of embodiments the reservoir space is adapted for application to the axilla of a person, preferably the reservoir space is adapted for application to the axilla of an adult male.

In a further set of embodiments there is provided a method of dispensing a volume of liquid for application to a skin surface including: providing a device as hereinbefore described comprising a container containing the liquid, pumping a volume of liquid from the container through the aperture formed in a the receptacle to the receptacle defining a reservoir space to accommodate the extracted volume of liquid wherein the reservoir space is adapted to substantially collapse when the volume of liquid is applied to the treatment surface.

In a preferred set of embodiments the liquid is a liquid pharmaceutical composition for application to at least one axilla of a person and the receptacle is adapted for spreading the liquid over the surface of the axilla of the person.

In a further set of embodiments there is provided a method of transdermal administration of a physiologically active agent to a subject including providing a device as hereinbefore described wherein a liquid comprising the pharmaceutically active agent is contained in the container; pumping a volume of liquid from the container through the aperture formed in a the receptacle to the receptacle defining a reservoir space to accommodate the extracted volume of liquid wherein the reservoir space is adapted to substantially collapse when the volume of liquid is applied to the treatment surface; and spreading the liquid over an area of skin in at least one axilla of the subject.

In another set of embodiments there is provided a method of increasing the testosterone blood level of a person in need thereof comprising applying to at least one axilla of the person a liquid comprising testosterone wherein the liquid is applied by a device hereinbefore described.

The liquid may take the form of a solution, lotion, gel, or cream. In one embodiment, the composition appears like a lotion. In this context, "lotion" is used in its broad descriptive sense to refer to a low- to medium-viscosity topical preparation intended for application to unbroken skin. By contrast, creams and gels have higher viscosity but are considered liquids. The terms lotion, creams and gels include singe phase preparations and multiphase preparations, that is preparations comprising a mixture, such as an emulsion, of immiscible liquids and/or a dispersion containing a solid in finely dispersed form in a liquid medium. The composition is often a true solution, but with increased viscosity so that its viscosity is more similar to that usually associated with a solution, lotion or gel. The thickener is preferably present in an amount to provide a viscosity of the composition greater than that of water up to 300 cps and more preferably in the range of from 10 to 40 centipoise.

In one set of embodiments the thickener is present in an amount in the range of from 0.01% to 10% w/v (preferably from 0.1% to 5% w/v of the liquid.

The liquid will preferably comprise a volatile liquid, a physiologically active agent and preferably a thickener.

The volatile liquid (also sometimes called a "volatile carrier" or "vehicle") may be any solvent that is pharmacologically suitable and many such solvents are known in the art. One of the advantages of the inclusion of a volatile solvent or volatile carrier is that it facilitates the composition to dry rapidly, allow the absorption of the active agent, and avoid the problems of accidentally dosing others by confining administration to a small area of skin, preferably the axilla. Preferably the volatile liquid is a solvent having a vapour pressure above 35 mm Hg at atmospheric pressure and normal skin temperature of 32 degrees Celsius. Preferably, the solvent is a lower alkyl alcohol (such as $C_2$ to $C_4$ alkanols) or a mixture of such alcohols. Suitable solvents include ethanol, ethyl acetate, isopropanol, acetone, ethyl formate, methyl acetate, methyl ethyl ketone, pentane and chloroform or mixture thereof in the range of about 40% to 99% v/v of the composition, preferably from 50% to 99% v/v, more preferably from 60% to 99% v/v, still more preferably from 70% to 99% v/v and most preferably from 80% to 99% v/v.

The more preferred volatile solvents are ethanol, isopropanol and mixtures thereof in an amount in the range of about 40 to 99% v/v of the composition, preferably from 50% to 99% v/v, more preferably from 60% to 99% v/v, still more preferably from 70% to 99% v/v and most preferably from 80% to 99% v/v.

The physiologically active agent may be selected from hormones and steroids such as testosterone, estrogen or progestin, female contraceptives and non steroidal anti-inflammatory agents. Physiologically active agents that may be used in the system of the present invention include any locally or systemically active agents which can be delivered through the skin to achieve a desired effect. The preferred classes of drugs are steroids and hormones (particularly steroidal hormones) and non-steroidal anti-inflammatory drugs (NSAIDS): NSAID means a drug whose principal mechanism of action associated with its therapeutic use is blocking the synthesis of prostaglandins by inhibiting cyclooxygenase, which converts arachidonic acid to cyclic endoperoxides, precursors of prostaglandins.

Suitable pharmacologically active compounds may be selected from:

non-steroidal anti-inflammatory drugs (NSAIDS) including their racemic mixtures or individual enantiomers where applicable. Suitable NSAIDS may be selected from the group consisting of salicylates such as aspirin, diflunisal and salsalate; propionic acid derivatives such as ibuprofen, dexibuprofen, naproxen fenoprofen, ketoprofen dexketoprofen, flurbiprofen, oxaprozin and loxoprofen; acetic acid derivatives such as indomethacin, tolmetin, sulindac, etodolac, ketorolac, diclofenac and nabumetone, enolic acid derivatives such as piroxicam, meloxicam, lysine clonixinate, tenoxicam, droxicam, lornoxicam and isoxicam; fenamates such as mefenamic acid, meclofenamic acid, flufenamic acid and tolfenamic acid; and coxibs such as celecoxib, parecoxib, etoricoxib, firocoxib and paracetamol. Preferred NSAIDS are selected from the group consisting of ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol and ketorolac;

Hormones and Steroids including:

estrogens such estradiol, estriol, estradiol benzoate, estradiol 17. beta.-cypionate, estradiol enanthate, estradiol propionate, estrone, ethinylestradiol, Fosfestrol, Dienestrol mestranol, stilboestrol, dienoestrol, epioestriol, estropipate diethylstilbestrol, chlorotrianisene, conjugated estrogenic hormones, polyestradiol phosphate and zeranol and mixtures thereof;

progesterone and progestins such as norethisterone, norethisterone acetate (also known as norethindrone acetate) gestodene, levonorgestrel, allylestrenol, anagestone, desogestrel, dimethisterone, dydrogesterone, ethisterone, ethynodiol, ethynodiol diacetate, etonogestrel, gestodene, ethinylestradiol, haloprogesterone, 17-hydroxy-16-methylene-progesterone, 17. alpha.-hydroxyprogesterone, lynestrenol, medroxyprogesterone, melengestrol, norethindrone, norethynodrel, norgesterone, gestonorone, norethisterone, norgestimate, norgestrel, levonorgestrel, norgestrienone, norvinisterone, pentagestrone, MENT (7-methyl-19-testosterone); norelgestromin, and trimigestone drospirenone, tibolone, and megestrol and mixtures thereof;

androgens and anabolic agents such as androisoxazole, androstenediol, bolandiol, bolasterone, clostebol, ethylestrenol. formyldienolone, 4-hydroxy-19-nortestosterone, methandriol, methenolone, methyltrienolone, nandrolone, norbolethone, oxymesterone, stenbolone and trenbolone. Androgenic steroids can include boldenone, fluoxymesterone, mestanolone, mesterolone, methandrostenolone, 17-methyltestosterone, 17-alpha.-methyltestosterone 3-cyclopentyl enol ether, norethandrolone, normethandrone, oxandrolone, oxymesterone, oxymetholone, prasterone, stanlolone, stanozolol, testosterone, testosterone 17-chloral hemiacetal, testosterone proprionate, testosterone enanthate, tiomesterone, dehydroepiandrosterone (DHEA), androstenedione (Andro): an androstenediol, androsterone, dihydrotestosterone (DHT) and androstanolone and derivatives thereof.

It is particularly preferred that the active is effective via the systemic circulation.

The amount of active present in the composition will depend on the desired response required and dose to be administered. Generally the active will be present at a concentration in the range of from 0.01% to 15% w/v of the liquid composition, preferably from 0.01% to 10% w/v of the liquid composition, more preferably from 0.1% to 8% w/v of the composition and most preferably from 0.1% to 5% w/v of the composition.

In one embodiment the pharmaceutically active agent comprises one or more steroidal hormones in a total amount of from 0.01% to 15% w/v of the liquid composition, preferably from 0.01% to 10% of the liquid composition, more preferably from 0.1% to 8% w/v of the liquid composition and most preferably from 0.1% to 5% w/v of the liquid composition.

In a further embodiment the pharmaceutical active comprises one or more non-steroidal anti-inflammatory drugs in a total amount of from 0.01% to 15% w/v of the liquid compositions, preferably from 0.01% to 10% w/v of the liquid composition, more preferably 0.1% to 8% w/v of the liquid composition and most preferably from 0.1% to 5% w/v of the liquid composition.

The preferred active agent is testosterone or a derivative thereof, which may be used in the treatment of testosterone deficiency in men and women and the conditions and diseases resulting therefrom. The composition may therefore comprise testosterone or a derivative thereof. There are number of closely related androgenic compounds which are synthetically derivatized from testosterone are known to provide the same or a similar physiologic activity. Such compounds include without limitation, testosterone salts, such as acetate, enanthate, cypionate, isobutyrate and propionate salts, undecanoate esters, cyproterone acetate, danazol, finasteride, fluoxymesterone, methyltestosterone, nandrolone decanoate, nandrolone phenpropionate, oxandrolone, oxymetholone, stanozolol, and testolactone.

In the case of androgens, particularly testosterone, the androgen is preferably present in an amount in the range of from 0.01% to 15% w/v of the liquid composition, preferably from 0.01% to 10% w/v of the liquid composition, more preferably from 0.1% to 8% w/v of the composition, still more preferably from 0.1% to 5% w/v of the composition such as about 0.5%, about 1%, about 1.5% or 2% w/v of the liquid composition.

Testosterone production in both men and women declines naturally with age. Testosterone deficiency may result from disease or damage to the hypothalamus, pituitary gland, or testicles that inhibits hormone secretion and testosterone production, and is also known as hypogonadism. Depending on age, insufficient testosterone production can lead to abnormalities in muscle and bone development, underdeveloped genitalia, and diminished virility.

Testosterone deficiency in men (hypogonadism) may be present at birth (congenital) or may develop later (acquired). It is classified by the location of its cause along the hypothalamic-pituitary-gonadal axis:

Primary, disruption in the testicles;

Secondary, disruption in the pituitary; and

Tertiary, disruption in the hypothalamus.

The most common congenital cause is Klinefelter's syndrome. This condition, which is caused by an extra X chromosome, results in infertility, sparse facial and body hair, abnormal breast enlargement (gynecomastia), and small testes.

Congenital hormonal disorders such as leutenizing hormone-releasing hormone (LHRH) deficiency and gonadotropin-releasing hormone (GnRH) deficiency (e.g., Kallmann's syndrome) also may cause testosterone deficiency.

Other congenital causes include absence of the testes (anorchism; also may be acquired) and failure of the testicles to descend into the scrotum (cryptorchidism).

Acquired causes of testosterone deficiency include chemotherapy; damage occurring during surgery involving the pituitary gland, hypothalamus, or testes; glandular malformation; head trauma that affects the hypothalamus; infection (e.g., meningitis, syphilis, mumps); isolated LH deficiency (e.g., fertile eunuch syndrome); radiation; testicular trauma; and tumors of the pituitary gland, hypothalamus, or testicles.

The invention may be used in the treatment of sexual dysfunction in men and women.

Androgen deficiency in women has been associated with an increased rate of sexual problems or complaints in a number of studies. These problems are frequently encountered in oophorectomized women and those with androgen deficiency from other causes. Hypoactive sexual desire disorder (HSDD) in women is the persistent or recurring deficiency (or absence) of sexual fantasies, thoughts and/or desire for, or receptivity to, sexual activity, which causes personal distress. The cause may be either physiological or psychological or a combination of both. Common physiological etiologies include hormone deficiencies, medications, and surgical interventions. Any disruption of the female hormonal milieu caused by these etiologies can result in decreased sexual desire. The lack of, or a decrease in, sexual desire may also be secondary to poor sexual arousal and response, or to pain associated with sexual activity. Another factor may be difficulty with inability to attain or maintain sufficient sexual excitement, a condition known as female sexual arousal disorder (FSAD).

In one set of embodiments the device containing a liquid comprising testosterone is for use in treatment of an adult male in need thereof. The adult male may be suffering from testosterone deficiency, hypogonadism or other condition in which testosterone therapy is beneficial.

Normal daily production of testosterone in normal young men ranges from 3-10 mg per day with diurnal variation (maximum ~7 am declining throughout the day). The aim of testosterone therapy in men is to deliver physiologic amounts of testosterone to the systemic circulation producing serum testosterone levels within the normal range for healthy men (e.g. 300-1050 ng/dL). The treatment may be used in testosterone deficient men to provide a testosterone levels within the normal range for healthy men (e.g. 300-1050 ng/dL).

Several clinical studies have demonstrated that in conditions such as female sexual dysfunction, testosterone administration, which is aimed at restoring testosterone levels to normal reproductive levels, is effective in improving sexual function. The studies to date suggest that systemic administration of doses ranging from 150 µg to 300 µg a day would be sufficient to return testosterone levels to mid- to high premenopausal levels in androgen deficient women.

In one embodiment, the invention is used to deliver a composition containing testosterone as the active agent to the axilla of a patient to result in a blood level of testosterone of at least a predetermined amount. In one embodiment, the predetermined amount is the normal range. In the case of testosterone, the blood level achieved is at least 200 ng/dL, preferably 300-1050 ng/dL. The invention may be used in the treatment of a wide variety of conditions responsive to testosterone therapy such as AIDS Wasting Syndrome, micropenis, somatopause, andropause, viropause, or androgen deficiency in adult males (ADAM), anemia from renal dialysis or chronic kidney disease, benign prostatic hyperplasia, acne, diabetes, infertility, periodontal disease, post anabolic steroid abuse, dry eyes, diabetic retinopathy, retinopathy, and Lupus Erythematosis decreased bone density (i.e. osteoporosis), hyperlipemia, predisposition toward prostate cancer, heart disease, angina, and hypertension.

In further embodiments, the invention may be used in a method of treatment of oestrogen and/or progestin deficiency, a method of treatment of chronic pain, and a method of treatment of anxiety related disorders.

The liquid composition may and preferably will contain a thickening agent. Examples of thickening agents include lipid thickeners such as beeswax, cetyl alcohol and stearyl alcohol; naturally derived thickeners such as celluloses and modified celluloses such as hydrolysed cellulose and cellulose ethers, gallactomannan gums such as guar gum and xanthan gum and gelatin; synthetic thickeners such as cross-linked acidic polymers (e.g. CARBOMER™ polymers) and polyacrylic acids cross-linked with polyalkenylether (e.g. CARBOPOL™ polymers), polyacrylamides and polyvinyl alcohol; salts such as magnesium aluminium silicates and polyvinyl pyrrolidone and cross linked polyvinyl pyrrolidone.

Preferred examples of thickening agents include polyvinyl alcohol (PVA); celluloses; modified cellulose and derivatives (such as hydroxypropyl cellulose (HPC) and hydroxypropylmethyl cellulose (HPMC)); polyvinyl pyrrolidone (PVP) (Povidone™); cross-linked polyvinyl pyrrolidone; ammonium acryloyldimethyltaurate/VP copolymer (e.g. Aristoflex AVC™); polyethylene glycol (PEG); acrylic acid polymer, polyacrylic acid, carboxyvinyl polymer (e.g. CARBOPOL™) and glycerin and glyceryl polyacrylate (e.g. HISPAGEL™).

The nature of the thickening agent depends not only on the agent itself, but also the proportion in which it is present and the presence or absence of other components. For example, a polymeric thickening agent may increase viscosity by virtue of the presence of cross-linking formed prior to or after inclusion in the composition. Cross-linking may be induced by an activator. For example, hydroxypropylmethylcellulose (HPMC) may optionally be used in a composition with an activator, in which the volatile solvent is a lower alkyl alcohol. The activator may, for example, be used in amounts such as 0.5% to 3% w/w or preferably at a concentration of about 2% w/w. A suitable activator would be sodium chloride.

The thickening agent will often be used to increase the viscosity of the composition containing a solution of the physiologically active agent in the volatile solvent. Given the nature of the volatile solvents, the solution will typically have very low viscosity. The purpose of the thickener is to increase the viscosity of the solution such that the composition is retained in the vicinity of the area of application (such as the axilla) for a brief period of time so as to permit increased uptake of the physiologically active agent at that site. The thickener preferably increases the viscosity to about that of a typical lotion (e.g., sunscreen), but not to the point where the composition becomes a gel. The thickener retains its activity in the context of the other components of the composition of the invention. In particular, the thickening agent must remain active and stable in this environment. In one embodiment the composition has a high alcohol content (for example, where the volatile solvent comprises primarily alcohol at greater than 80% v/v), the thickening agent should be effective in a high alcoholic environment. Having these requirements in mind, a skilled person can select several thickening agents from those known in the art. Desirably, a thickening agent also inhibits the solvent evaporation rate from the composition so as to enhance the so-called "solvent burst" of active agent into the skin at the site of application. In one embodiment the thickening agent includes polyvinylpyrrolidone or (PVP) (e.g. Povidone™).

It will be appreciated by one skilled in the art that the amount of thickening agent required is a question of degree and compromise with other parameters. It is also known that many thickening agents have peak activity at a particular concentration, and that activity may drop off with higher or lower percentage concentrations. For example, in one embodiment where the composition comprises over 80% alcohol and the thickening agent used is PVP, the desirable concentration of PVP is between 1 and 3%.

The thickening agent may provide a gel by forming a matrix within and around the composition they are in.

In some embodiments, the thickening agent is an antiperspirant or the composition further includes an antiperspirant and/or a deodorant.

Despite the inherent antiperspirant and/or deodorant properties of the composition, the composition may be optionally administered with deodorant and antiperspirant additives that do not interfere with the active. In another form, the liquid may comprise at least one physiologically active agent; and at least one volatile solvent; and at least one antiperspirant or deodorant.

In one embodiment, the composition comprises an antiperspirant agent. The antiperspirant agent may be any suitable substance that reduces or inhibits the production of sweat. In some instances, an antiperspirant agent can also provide deodorancy benefits.

In one embodiment, the composition may comprise a penetration enhancer. The penetration enhancer is also sometimes called an "absorption" enhancer. Suitable dermal penetration enhancers are described in U.S. Pat. No. 6,299,900, WO 2006/128255 and WO 2009/055860, the contents of each of which are herein incorporated by reference. The preferred dermal penetration enhancers include: fatty acids, fatty acid esters, fatty alcohols, glycols and glycol esters, 1,3-dioxolanes and 1,3-dioxanes, macrocyclic ketones and lactones containing at least 12 carbon atoms, oxazolidinones and oxazolidinone derivatives, alkyl-2-(N,N-disubstituted amino)-alkanoate esters, (N,N-disubstituted amino)-alkanol alkanoates, sunscreen esters and mixtures thereof. These include the compounds being safe skin-tolerant ester sunscreens of formula:

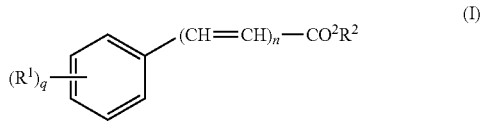

(I)

wherein $R^1$ is hydrogen, lower alkyl, lower alkoxy, halide, hydroxy or $NR^3R^4$;

$R^2$ is long chain alkyl;

$R^3$ and $R^4$ are each independently hydrogen, lower alkyl or $R^3$ and $R^4$ together with the nitrogen atom to which they are attached form a 5- or 6-membered heterocyclic ring;

n is 0 or 1; and q is 1 or 2.

More preferably the dermal penetration enhancer is selected from the list including oleic acid, oleyl alcohol, dipropylene glycol, cyclopentadecanone (CPE-218™), pentadecalactone, sorbitan monooleate, glycerol monooleate, propylene glycol monolaurate, methyl laurate, polyethylene glycol (PEG, preferably of molecular weight no more than 300), polyethylene glycol monolaurate, 2-n-nonyl 1,3-dioxolane (SEPA™), dodecyl 2-(N,N-dimethylamino)-propionate (DDAIP) or its salt derivatives, 2-ethylhexyl 2-ethylhexanoate, isopropyl myristate, dimethyl isosorbide, 4-decyloxazolidinon-2-one (SR-38™, TCPI, Inc.), 3-methyl-4-decyloxazolidinon-2-one, octyl dimethyl-para-aminobenzoate, octyl para-methoxycinnamate, octyl salicylate and mixtures thereof.

Still more preferably the penetration enhancer is octyl para-methoxycinnamate, octyl salicylate, polyethylene glycol of molecular weight no more than 300 or mixture thereof and most preferably the penetration enhancer is octyl salicylate optionally in composition with polyethylene glycol of molecular weight no more than 300.

The concentration of absorption/penetration enhancer may be in the range from 10-10,000 weight percent of absorption/penetration enhancer based upon the weight of active ingredient. The ratio of penetration enhancer to active ingredient may vary considerably and will be governed as much as anything, by the pharmacological results that are required to be achieved. In principle, it is desirable that as little absorption enhancer as possible is used. However, it is most preferable that the penetration enhancer be in the range from 0.01% to 15% w/v of the total composition. More preferable the penetration enhancer is from 0.1% to 10% w/v of the composition and most preferably from 0.5% to 8% w/v of the composition. In particularly preferred set of embodiments the penetration enhancer is octyl salicylate present in an amount of from 0.01% to 15% w/v of the composition (preferably from 0.1% to 10% w/v of the composition and most preferably from 0.5% to 8% w/v of the composition).

Preferably the composition is non-occlusive, in that in the broadest sense, the composition is not trapped to the skin, or the skin is not closed to the atmosphere, by means of a patch device, fixed reservoir, application chamber, tape, bandage, sticking plaster, or the like, which remains on the skin at the site of application for a prolonged length of term. Such devices tend to be uncomfortable for the wearer or can be embarrassing or unsightly.

In one embodiment, the composition consists essentially of one physiologically active agent; one volatile solvent; and one thickener, each as described above. Preferably, it further includes a penetration enhancer as described above. In one embodiment, the thickener is an antiperspirant, and the composition optionally also includes a deodorant. Each of these embodiments may or may not also include water.

In another embodiment, the composition may include at least one additional active agent and/or at least one additional inactive agent. In a different embodiment, the composition does not include a herbal extract (or like component), whether as a physiologically active agent or otherwise.

The composition may be applied to a wide range of areas of the skin depending on the nature of the drug and liquid composition. When the physiologically active agent is an NSAID the device may be used to apply the liquid composition to relieve pain associated with muscle or joint injuries such as sprains, strains, or sports injuries. Examples of typical joints on which the liquid composition containing NSAIDS may be applied include the knee, shoulder, elbow, ankle or toes of a subject. In the case of steroidal hormones the device may be used to apply the liquid composition to one or more areas of the upper body such as the chest, upper arms, forearms, and one or both axilla. In the case of use of the device where the liquid comprised steroidal hormones such as testosterone application to one or both axilla is particularly preferred. The device in one embodiment is used in application of testosterone or similar androgen to at least one axilla of an adult male subject in need thereof.

Suitable forms of the liquid include for example lotions, creams or gels. The composition may be applied in an occlusive or non-occlusive manner. It is preferred that the composition is applied in a non-occlusive manner and in the most preferred embodiment the composition is formulated for application as a lotion, gel or cream. Generally, the properties of the composition are such that it can be readily dispensed and spread by the implement of the invention. The composition can be formulated by adding suitable carriers, excipients and thixotropic agents which are inert to the active to facilitate dispensing and spreading of the composition and thus delivery of the composition to the skin for transdermal administration of the active agent.

The composition may further comprise additional components that will facilitate its preparation into forms suitable for application to the axilla of a subject. Examples of additional components include but are not limited to surfactants, buffers, solvents and propellants. In one set of embodiments the liquid composition comprises:

(a) pharmaceutically effective amount (preferably in the range of from 0.01% to 15% w/v of the liquid composition, more preferably from 0.01% to 10% w/v of the liquid composition, more preferably from 0.1% to 8% w/v of the composition and most preferably from 0.1% to 5% w/v of the composition) of physiologically active agent;

(b) one or more lower alcohols ($C_2$ to $C_4$ alkanols, preferably selected from the group consisting of ethanol, isopropanol and mixtures thereof) in and amount in the range of from 40% to 99% v/v (preferably from 50% to 99% v/v, more preferably from 60% to 99% v/v, still more preferably from 70% to 99% v/v and most preferably from 80% to 99% v/v);

(c) one or more penetration enhancers (preferably selected from the group consisting of oleic acid, oleyl alcohol, dipropylene glycol cyclopentadecanone (CPE-218™), pentadecalactone, sorbitan monooleate, glycerol monooleate, polyethylene glycol (particularly of molecular weight no more than 300) propylene glycol monolaurate, polyethylene glycol monolaurate, 2-n-nonyl 1,3-dioxolane (SEPA™), dodecyl 2-(N,N-dimethylamino)-propionate (DDAIP) or its salt derivatives, 2-ethylhexyl 2-ethylhexanoate, isopropyl myristate, dimethyl isosorbide, 4-decyloxazolidinon-2-one (SR-38™, TCPI, Inc.), 3-methyl-4-decyloxazolidinon-2-one, octyl dimethyl-para-aminobenzoate, octyl para-methoxycinnamate, octyl salicylate and mixtures thereof and most preferably octyl salicylate in an amount of from 0.01% to 15% w/v (preferably from 0.01% to 10% w/v of the liquid composition, more preferably from 0.1% to 8% w/v of the composition, still more preferably from 0.1% to 5% w/v of the composition) of the composition; and optionally (d) a thickening agent.

In one set of embodiments the liquid composition comprises:

(a) at least one physiologically active agent selected from the group consisting of steroidal hormones and non-steroidal anti-inflammatory drugs in a total amount of 0.01% to 15% w/v of the liquid composition;

(b) ethanol, isopropanol or a mixture thereof in a total amount of 60% to 99% v/v of the liquid composition;

(c) one or more penetration enhancers selected from the group consisting of oleic acid, oleyl alcohol, dipropylene glycol, cyclopentadecanone (CPE-218™), sorbitan monooleate, glycerol monooleate, propylene glycol monolaurate, methyl laurate, polyethylene glycol of molecular weight no more than 300, polyethylene glycol monolaurate, 2-n-nonyl 1,3-dioxolane (SEPA™), dodecyl 2-(N,N-dimethylamino)-propionate (DDAIP) or its salt derivatives, 2-ethylhexyl 2-ethylhexanoate, isopropyl myristate, dimethyl isosorbide, 4-decyloxazolidinon-2-one (SR-38™, TCPI, Inc.), 3-methyl-4-decyloxazolidinon-2-one, octyl dimethyl-para-aminobenzoate, octyl para-methoxycinnamate, octyl salicylate and mixtures thereof in a total amount of from 0.01 to 15% w/v of the liquid composition;

(d) optionally a thickening agent.

In one set of embodiments the composition comprises:

(a) steroidal hormone in an amount of from 0.01% to 15% w/v, preferably in the range of 0.01% to 10% w/v, more preferably in the range 0.1% to 8% w/v and most preferably in the range 0.1% to 5% w/v of the composition;

(b) one or more $C_2$ to $C_4$ alkanols, preferably selected from ethanol, isopropanol and mixtures thereof in a total amount of from 50% to 99% v/v (preferably 60% to 99% v/v, still more preferably 70% to 99% v/v and most preferably from 80% to 99% v/v;

(c) one or more penetration enhancers selected from the group consisting of octyl salicylate, dipropylene glycol, PEG of molecular weight no more than 300 or a mixture thereof in a total amount of from 0.01 to 15% w/v, preferably 0.1% to 10% w/v, more preferably 0.5% to 8% w/v;

(d) optionally a thickening agent.

The steroidal hormone in one set of embodiments is testosterone. Accordingly the liquid in one set of embodiments, comprises:

(a) testosterone in an amount of 0.01% to 15% w/v (preferably 0.01% to 10% w/v and more preferably 0.1% to 8% w/v) of the liquid composition;

(b) ethanol, isopropanol or a mixture thereof in a total amount of 60% to 99% v/v (preferably 70% to 99% v/v and more preferably 80% to 99% v/v) of the liquid composition;

(c) octyl salicylate penetration enhancer in an amount from 0.01% to 15% w/v (preferably from 0.1% to 10% w/v and more preferably 0.1 to 8% w/v) of the liquid composition; and (d) optionally a thickener.

In a further set of embodiments, the composition comprises:

(a) non-steroidal anti-inflammatory drug in an amount of from 0.01% to 15% w/v, preferably in the range of 0.01% to 10% w/v, more preferably in the range 0.1% to 8% w/v and most preferably in the range 0.1% to 5% w/v of the liquid composition;

(b) one or more $C_2$ to $C_4$ alkanols, preferably selected from ethanol, isopropanol and mixtures thereof in a total amount of from 50% to 99% v/v (preferably 60% to 99% v/v, still more preferably 70% to 99% v/v and most preferably from 80% to 99% v/v of the liquid composition;

(c) octyl salicylate, PEG of molecular weight no more than 300 or a mixture thereof in a total amount of from 0.01 to 15% w/v, preferably 0.1% to 10% w/v, more preferably 0.5% to 8% w/v;

(d) optionally a thickening agent.

More specific examples of liquid compositions include the following:

0.5% to 5% w/v testosterone;

0.1% to 10% w/v octyl salicylate;

70% to 99% v/v volatile liquid selected from ethanol isopropanol and mixtures thereof; and thickening agent preferably in an amount to provide a viscosity in the range of from the viscosity of water to 300 centipoise, preferably 10 to 40 centipoise.

In the most preferred example the liquid compositions for delivery using the device comprises:

2% w/v testosterone

5% w/v octisylate

2% w/v polyvinylpyrrolidone;

30% v/v isopropyl alcohol; and

To 100% v/v with 95% ethanol.

In one embodiment the device is adapted to dispense a volume of liquid comprising testosterone active agent in an amount of from 5 to 120 mg testosterone (preferably from 10 to 60 mg and most preferably about 30 mg) on each actuation of the pump corresponding with full displacement of the pump head.

In one embodiment, the composition comprises a volatile carrier which is isopropyl alcohol, a penetration enhancer which is octisalate, an active agent which is testosterone and a thickening agent.

In another embodiment, the composition may further include a second active agent to provide the composition with additional usage benefits. The second active agent may be selected from any one of the active agents listed above, or herbal extracts and/or cosmetic agents (such as, age spot and keratose removing agents, anti-aging agents, antioxidants, and hydroxy acids).

In yet another embodiment, the composition may further comprise one or more inactive agents. Such inactive ingredients may be referred to as "additives". Examples of such additives include but are not limited to, humectants, deodorant agents, antiperspirants, pH adjusting agents, preservatives, emulsifiers, occlusive agents (including without limitation patches and film formers), solubilizing agents, colorants, and surfactants (including without limitation anionic surfactants).

The invention is described with reference to the following Examples. It is to be understood that the Examples are provided by way of illustration of the invention and are not limiting to the scope of the invention.

EXAMPLES

The device for dispensing and applying a volume of liquid to treat a surface as shown in FIGS. 1 to 9 may be used to apply a liquid composition comprising a pharmaceutically active agent in accordance with Composition Examples 1 to 31.

The device of FIGS. 1 to 9 may be used with a volume of liquid formulation of Composition Examples 1 to 31 in the container (3). Referring to the drawings, the collar (7) may be rotated with respect to the base (8) to cause operation of pump (9) to force the liquid composition out of the container (3) and into reservoir space (10) defined by receptacle (5). The device, held in the hand of the subject, is applied using the receptacle to spread the liquid in the region of the body, preferably to one or more of the axilla.

Suitable pumps may dispense volumes in the range of 1 ml to 2 ml of the liquid compositions. Most preferred is a pump which dispenses approximately 1.5 ml of liquid (+/− 15%). Typically the pump may be configured to dispense the required doses with between one and four pump actuations.

Composition Examples 1-3

The following compositions (composition 1 being the most preferred) may be used in treatment of testosterone deficiency in adult males by application using the device to deliver 1 ml to 2 ml of liquid composition to one or both axilla.

Composition Example 1

2% w/v testosterone
5% w/v octisalate
2% w/v povidone K-90
30% v/v isopropyl alcohol
to 100% v/v with 95% ethanol Composition Example 2

2% w/v testosterone
5% w/v octisalate
2% w/v povidone K-90
30% v/v isopropyl alcohol
2.5% w/v polyethylene glycol 200
to 100% v/v with 95% ethanol (optimized formulation-Report-341)

Composition Example 3

2% w/v testosterone
5% w/v octisalate
2% w/v povidone K-90
2.5% w/v polyethylene glycol 200
to 100% v/v with isopropyl alcohol (optimized formulation-Report-341)

Composition Examples 4-14

The following compositions containing NSAID active agents may be used to provide analgesic, antipyretic and/or anti-inflammatory treatments for subjects in need thereof by application of the composition to an area of the body surface, such as the axilla or joints such as the elbow, knee or toes.

Composition Example 4

1% w/v diclofenac
5% w/v octisalate
2.5% w/v polyethylene glycol 200
to 100% v/v with isopropyl alcohol Composition Example 5

1-4.5% w/v diclofenac
5% w/v octisalate
2.5% w/v polyethylene glycol 200
to 100% v/v with isopropyl alcohol Composition Example 6

1-4.5% w/v diclofenac
5% w/v octisalate
2.5% w/v polyethylene glycol 200
2% w/v povidone K-90
to 100% v/v with isopropyl alcohol Composition Example 7

3.2-5% w/v ibuprofen
5% w/v octisalate
2.5% w/v polyethylene glycol 200
to 100% v/v with isopropyl alcohol Composition Example 8

3.2-5% w/v ibuprofen
5% w/v octisalate
2.5% w/v polyethylene glycol 200
2% w/v povidone K-90
to 100% v/v with isopropyl alcohol Composition Example 9

5% w/v ketoprofen
5% w/v octisalate
2.5% w/v polyethylene glycol 200
to 100% v/v with isopropyl alcohol

Composition Example 10

5% w/v ketoprofen
5% w/v octisalate
2.5% w/v polyethylene glycol 200
2% w/v povidone K-90
to 100% v/v with isopropyl alcohol

Composition Example 11

2.5% w/v naproxen
5% w/v octisalate
7.5% w/v polyethylene glycol 200
to 100% v/v with isopropyl alcohol

Composition Example 12

5% w/v naproxen
5% w/v octisalate
7.5% w/v polyethylene glycol 200
2% w/v povidone K-90
to 100% v/v with isopropyl alcohol

Composition Example 13

5% w/v naproxen sodium
5% w/v octisalate
7.5% w/v polyethylene glycol 200
to 100% v/v with 95% isopropyl alcohol

Composition Example 14

5% w/v naproxen sodium
5% w/v octisalate
7.5% w/v polyethylene glycol 200
2% w/v povidone K-90
to 100% v/v with 95% isopropyl alcohol

Composition Examples 15-21

The following compositions containing steroidal hormones may be used in female contraception by application of the composition to the axilla.

Composition Example 15

1.35% w/v nestorone
0.35% w/v estradiol
5% w/v octisalate
to 100% v/v with isopropyl alcohol

Composition Example 16

2.0% w/v nestorone
0.35% w/v estradiol
5% w/v octisalate
5% w/v dipropylene glycol
to 100% v/v with isopropyl alcohol

Composition Example 17

1.60% w/v nestorone
0.35% w/v ethinyl estradiol
5% w/v octisalate
to 100% v/v with isopropyl alcohol

Composition Example 18

1.35% w/v nestorone
0.35% w/v ethinyl estradiol
5% w/v octisalate
5% w/v polyethylene glycol 200
to 100% v/v with isopropyl alcohol

Composition Example 19

0.5% w/v etonogestrel
5% w/v octisalate
5% w/v dipropylene glycol
to 100% v/v with isopropyl alcohol

Composition Example 20

0.5% w/v etonogestrel
5% w/v octisalate
10% w/v dipropylene glycol
to 100% v/v with isopropyl alcohol

Composition Example 21

0.5% w/v etonogestrel
5% w/v octisalate
5% w/v polyethylene glycol 200
to 100% v/v with isopropyl alcohol

Composition Examples 22-31

The following composition containing steroidal hormones may be used in hormone replacement therapy in women in need thereof.

Composition Example 22

1.7% w/v estradiol
8.5% w/v octisalate
to 100% v/v with 95% ethanol

Composition Example 23

0.5% w/v estradiol
5% w/v octisalate
to 100% v/v with 95% ethanol
0.25% w/v estradiol
to 100% v/v with isopropyl alcohol

Composition Example 24

0.25% w/v estradiol
5% w/v octisalate
to 100% v/v with 95% ethanol

Composition Example 25

0.25% w/v estradiol
5% w/v octisalate
5% w/v triacetin
to 100% v/v with isopropyl alcohol

Composition Example 26

0.25% w/v estradiol
5% w/v octisalate
5% w/v poly norethindrone acetate ethylene glycol 200
to 100% v/v with isopropyl alcohol Composition Example 27

5% w/v testosterone
8% w/v octisalate
to 100% v/v with 95% ethanol

Composition Example 28

4% w/v testosterone
5% w/v octisalate
1% w/v polyethylene glycol 200
to 100% v/v with isopropyl alcohol Composition Example 29

1% w/v testosterone
5% w/v octisalate
1% w/v polyethylene glycol 200
to 100% v/v with isopropyl alcohol Composition Example 30

2.8% w/v norethindrone acetate
0.18% w/v estradiol
5% w/v octisalate
5% w/v polyethylene glycol 200
to 100% v/v with isopropyl alcohol Composition Example 31

2.5% w/v norethindrone acetate
0.09% w/v estradiol
5% w/v octisalate
5% w/v polyethylene glycol 200
to 100% v/v with isopropyl alcohol
Povidone K-90 is a polyvinylpyrrolidone of average Mw of 360,000.

Various alterations and/or additions may be introduced to the device as hereinbefore described without departing from the spirit or ambit of the invention.

Future patent applications may be filed on the basis of or claiming priority from the present application. It is to be understood that the following provisional claims are provided by way of example only, and are not intended to limit the scope of what may be claimed in any such future application. Features may be added to or omitted from the provisional claims at a later date so as to further define or re-define the invention.

The invention claimed is:

1. A device for dispensing and applying a volume of liquid to a treatment surface, the device having an axis and including: a container for containing the liquid, a pump for extracting the volume of liquid from the container, an actuator for operating the pump, a receptacle defining a reservoir space while accommodating the extracted volume of liquid which substantially collapses when the volume of liquid is applied to the treatment surface, the receptacle having an aperture formed in a floor thereof through which the volume of liquid enters the reservoir space, the pump includes a head and a body with the head being movable in the direction of the axis so as to induce the volume of liquid to be expelled out of the head of the pump, the head is movable towards the body when inducing the volume of liquid to be expelled out of the head of the pump, the floor of the receptacle being resiliently deformable and operatively associated with the pump head so as to deform when the head is moved, the reservoir space has a depth, and the floor of the receptacle is movable with the pump head so that the depth of the reservoir space increases when the head is moved towards the body.

2. A device according to claim 1 wherein the receptacle includes a wall surrounding the floor, at least the wall of the receptacle is resiliently deformable so that in an erect condition it defines at least in part the reservoir space and resiliently deforms when the receptacle collapses.

3. A device according to claim 2 wherein the floor and wall are formed from a membrane.

4. A device according to claim 1 including a diffuser which diffuses the liquid as it enters the reservoir space.

5. A device according to claim 4 wherein the diffuser includes a single inlet and multiple outlets to guide the liquid across the floor of the reservoir space.

6. A device according to claim 5 wherein the outlets are oriented relative to the inlet so as to cause the liquid to change direction as it travels from the inlet to the outlets.

7. A device according to claim 1 wherein the actuator includes a base which is fixed relative to the container, a rotatable member that is rotatable relative to the base, and a shuttle that operatively interacts with the pump, and rotates with the rotatable member, and moves relative to the base in the axial direction when the pump extracts the volume of liquid.

8. A device according to claim 7 including a rack and pawl mechanism associated with the rotatable member and the base to configured to hinder the rotation of the rotatable member in a non-preferred direction.

9. A device according to claim 8 wherein the rack and pawl mechanism is configured to cause a greater level of hindrance to rotation of the rotatable member in the non-preferred direction when the actuator is in a rest position.

10. A device according to claim 9 wherein the rack includes a plurality of teeth of one size and one tooth that has a larger trailing edge, wherein the interaction of the pawl with the larger trailing edge causes said greater level of hindrance.

11. A device according to claim 10 wherein said larger trailing edge is at least 40% greater in depth than a trailing edge of a majority of the teeth.

12. A device according to claim 7 wherein the actuator includes a cam means so that rotation of the rotatable member causes axial movement of the shuttle from a first position toward a second position.

13. A device according to claim 12 wherein the cam means includes a cam surface on the shuttle and a cam follower on the base, wherein the cam follower moves along the cam surface on rotation of the rotatable member.

14. A device according to claim 13 wherein the cam surface is configured to interact with the cam follower so as to reduce resistance on the shuttle returning to the first position as the actuator approaches a rest position.

15. A device according to claim 14 wherein the cam surface is shaped with an end portion which is aligned substantially vertically so as to permit the shuttle to return to the first position before the actuator reaches the rest position.

16. A device according to claim 15 wherein the shuttle and rotatable member include guide means to limit movement of the shuttle in the axial direction relative to the rotatable member.

17. A device according to claim 13 wherein including a stop means for preventing the shuttle from moving in the axial direction unless by way of rotation of the rotatable member.

18. A device according to claim 1 wherein the pump is a positive displacement pump and the container includes a relatively rigid outer shell and a relatively collapsible inner lining, whereby the liquid is retained in the lining which collapses upon operation of the pump.

19. A device according to claim 1 wherein the treatment surface is an axilla area of a user's skin.

20. A device according to claim 1 wherein the container contains the liquid which is in the form of a composition including a physiologically active agent.

21. A device according to claim 20 wherein the physiological active agent includes at least one agent selected from steroidal hormones and non-steroidal anti-inflammatory drugs.

22. A device for dispensing and applying a volume of liquid to a treatment surface, the device having an axis and including: a container for containing the liquid, a pump for extracting the volume of liquid from the container, an actuator for operating the pump, a receptacle defining a reservoir space while accommodating the extracted volume of liquid which substantially collapses when the volume of liquid is applied to the treatment surface, the receptacle having an aperture formed in a floor thereof through which the volume of liquid enters the reservoir space, wherein the reservoir space has a depth, and the floor of the receptacle is movable with operation of the pump head so that the depth of the reservoir space increases while the liquid enters the reservoir space.

23. A system for transdermal administration of a physiologically active agent from a liquid the system comprising a device according to claim 1 wherein the container contains a liquid composition comprising the physiologically active agent.

24. A system according to claim 23 wherein the reservoir space is adapted for application to the axilla of an adult male.

25. A system according to claim 23 wherein the liquid composition comprises:
    (a) pharmaceutically effective amount of a physiologically active agent;
    (b) one or more lower alcohols in and amount in the range of from 40% to 99% v/v;
    (c) one or more penetration enhancers in an amount of from 0.01% to 15% w/v of the composition; and optionally (d) a thickening agent.

26. A system according to claim 23 wherein the liquid comprises:
    (a) A steroidal hormone or non-steroidal anti-inflammatory drug in an amount of 0.01% to 15% w/v of the liquid composition;
    (b) ethanol, isopropanol or a mixture thereof in a total amount of 60% to 99% v/v of the liquid composition;
    (c) one or more penetration enhancers selected from the group consisting of dipropylene glycol, polyethylene glycol of molecular weight no more than 300 and octyl salicylate and mixtures thereof in a total amount of from 0.01% to 15% w/v of the liquid composition;
    (d) optionally a thickening agent.

27. A system according to claim 23 wherein the liquid comprises:
    (a) testosterone in an amount of 0.01% to 15% w/v of the liquid composition;
    (b) ethanol, isopropanol or a mixture thereof in a total amount of 60% to 99% v/v of the liquid composition;
    (c) octyl salicylate penetration enhancer in an amount from 0.01% to 15% w/v of the liquid composition; and
    (d) optionally a thickener.

28. A system according to claim 23 wherein the liquid comprises a thickener selected from the group consisting of polyvinyl alcohol (PVA); celluloses; modified cellulose and derivatives; polyvinyl pyrrolidone (PVP); cross-linked polyvinyl pyrrolidone; ammonium acryloyldimethyltaurate/VP copolymer; polyethylene glycol (PEG); acrylic acid polymer, polyacrylic acid, carboxyvinyl polymer and glycerin and glyceryl polyacrylate.

29. A system according to claim 23 wherein the liquid comprises a thickener in an amount to provide a viscosity in the range of from the viscosity of water to 300 centipoise.

30. A system according to claim 23 wherein the thickener is present in an amount in the range of from 0.01% to 10%.

31. A system according to claim 23 wherein the liquid is for application to at least one axilla of a person and the receptacle is adapted for spreading the liquid over the surface of the axilla of the person.

32. A method of transdermal administration of a physiologically active agent to a subject including providing a device according to claim 1 wherein a liquid comprising the pharmaceutically active agent is contained in the container; pumping a volume of liquid from the container through the aperture formed in a the receptacle to the receptacle defining a reservoir space to accommodate the extracted volume of liquid wherein the reservoir space is adapted to substantially collapse when the volume of liquid is applied to the treatment surface; spreading the liquid over an area of skin in at least one axilla of the subject.

33. A method according to claim 32 wherein the reservoir space is adapted for application to the axilla, preferably the axilla of an adult male.

34. A method according to claim 32 wherein the liquid composition comprises:
    (a) pharmaceutically effective amount of an active agent;
    (b) one or more $C_2$ to $C_4$ alkanols in and amount in the range of from 40% to 99% v/v;
    (c) one or more penetration enhancers in an amount of from 0.01% to 15% w/v of the composition; and optionally
    (d) a thickening agent.

35. A method according to claim 32 wherein the liquid comprises:
    (a) at least one physiologically active agent selected from the group consisting of steroidal hormones and non-steroidal anti-inflammatory drugs in a total amount of 0.01% to 15% w/v of the liquid composition;
    (b) ethanol, isopropanol or a mixture thereof in a total amount of 60% to 99% v/v of the liquid composition;
    (c) one or more penetration enhancers selected from the group consisting of oleic acid, oleyl alcohol, dipropylene glycol, cyclopentadecanone, sorbitan monooleate, glycerol monooleate, propylene glycol monolaurate, polyethylene glycol of molecular weight no more than 300, polyethylene glycol monolaurate, 2-n-nonyl 1,3-dioxolane, dodecyl 2-(N,N-dimethylamino)-propionate (DDAIP) or its salt derivatives, 2-ethylhexyl 2-ethylhexanoate, isopropyl myristate, dimethyl isosorbide, 4-decyloxazolidinon-2-one, 3-methyl-4-decyloxazolidinon-2-one, octyl dimethyl-para-aminobenzoate, octyl para-methoxycinnamate, octyl salicylate and mixtures thereof in a total amount of from 0.01 to 15% w/v of the liquid composition;
    (d) optionally a thickening agent.

36. A method according to claim 32 wherein the liquid comprises:
    (a) a physiologically active agent selected from steroidal hormones and non-steroidal anti-inflammatory drugs in a total amount of 0.01% to 15% w/v of the liquid composition;

(b) ethanol, isopropanol or a mixture thereof in a total amount of 60% to 99% v/v of the liquid composition;
(c) penetration enhancer selected from octyl salicylate, dipropylene glycol and polyethylene glycol of molecular weight no more than 300 in a total amount from 0.01% to 15% w/v of the liquid composition; and
(d) optionally a thickener.

37. A method according to claim 32 wherein the liquid comprises a thickener selected from the group consisting of polyvinyl alcohol (PVA); celluloses; modified cellulose and derivatives; polyvinyl pyrrolidone (PVP); cross-linked polyvinyl pyrrolidone; ammonium acryloyldimethyltaurate/VP copolymer; polyethylene glycol (PEG); acrylic acid polymer, polyacrylic acid, carboxyvinyl polymer and glycerin and glyceryl polyacrylate.

38. A method according to claim 32 wherein the liquid comprises a thickener in an amount to provide a viscosity in the range of from the viscosity of water to no more than 300 centipoise.

39. A method according to claim 32 wherein the thickener is present in an amount in the range of from 0.01% to 10%.

40. A method according to claim 32 wherein the physiologically active agent is testosterone and the subject is a male suffering testosterone deficiency.

41. A method according to claim 40 wherein the liquid is configured to restore a serum testosterone level in the range of from 300 to 1050 ng/dl.

42. A method of dispensing a volume of liquid for application to a skin surface including: providing a device according to claim 1 comprising a container containing the liquid, pumping a volume of liquid from the container through the aperture formed in the floor of the receptacle to the receptacle defining a reservoir space to accommodate the extracted volume of liquid wherein the reservoir space is adapted to substantially collapse when the volume of liquid is applied to the treatment surface.

43. A method according to claim 42 wherein the reservoir space is adapted for application to an axilla of an adult male.

44. A method of increasing the testosterone blood level of a person in need thereof comprising applying to at least one axilla of the person a liquid comprising testosterone wherein the liquid is applied by a device according to claim 1 and the liquid comprises:
(a) testosterone in an amount of 0.01% to 15% of the liquid composition;
(b) one or more $C_2$ to $C_4$ alkanols in and amount in the range of from 40% to 99% v/v;
(c) one or more penetration enhancers in an amount of from 0.01% to 15% w/v of the composition; and optionally
(d) a thickening agent.

45. A method according to claim 44 wherein the liquid comprises:
(b) ethanol, isopropanol or a mixture thereof in a total amount of 60% to 99% v/v of the liquid composition;
(c) one or more penetration enhancers selected from the group consisting of dipropylene glycol, polyethylene glycol of molecular weight no more than 300, octyl salicylate and mixtures thereof in a total amount of from 0.01% to 15% w/v of the liquid composition;
(d) optionally a thickening agent.

46. A method according to claim 44 wherein the liquid comprises:
(a) testosterone in an amount of 0.01% to 15% w/v of the liquid composition;
(b) ethanol, isopropanol or a mixture thereof in a total amount of 60% to 99% v/v of the liquid composition;
(c) octyl salicylate penetration enhancer is an amount from 0.01% to 15% w/v of the liquid composition; and
(d) optionally a thickener.

47. A method according to claim 44 wherein the liquid comprises a thickener selected from the group consisting of polyvinyl alcohol (PVA); celluloses; modified cellulose and derivatives; polyvinyl pyrrolidone (PVP); cross-linked polyvinyl pyrrolidone; ammonium acryloyldimethyltaurate/VP copolymer; polyethylene glycol (PEG); acrylic acid polymer, polyacrylic acid, carboxyvinyl polymer and glycerin and glyceryl polyacrylate.

48. A method according to claim 44 wherein the liquid comprises a thickener in an amount to provide a viscosity in the range of from the viscosity of water no more than 300 centipoise.

49. A method according to claim 44 wherein the thickener is present in an amount in the range of from 0.01% to 10% of the liquid.

50. A method according to claim 44 wherein the subject is a male suffering testosterone deficiency.

51. A method according to claim 50 wherein the liquid is configured to restore a serum testosterone level in the range of from 300 to 1050 ng/dl.

* * * * *